US008759052B2

(12) United States Patent
Bach et al.

(10) Patent No.: US 8,759,052 B2
(45) Date of Patent: Jun. 24, 2014

(54) PROCESS FOR PRODUCING BIOGAS

(75) Inventors: Jan Bach, Hannover (DE); Jorg Burgstaler, Schwerin (DE); Denny Wiedow, Lambrechtshagen (DE); Frederik Degraeve, Alpen (DE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 13/696,627

(22) PCT Filed: May 10, 2011

(86) PCT No.: PCT/EP2011/057561
§ 371 (c)(1),
(2), (4) Date: Nov. 7, 2012

(87) PCT Pub. No.: WO2011/141484
PCT Pub. Date: Nov. 17, 2011

(65) Prior Publication Data
US 2013/0059357 A1 Mar. 7, 2013

(30) Foreign Application Priority Data
May 10, 2010 (EP) .................................. 10162425

(51) Int. Cl.
C12P 5/02 (2006.01)
(52) U.S. Cl.
USPC .......................................... 435/167; 435/266
(58) Field of Classification Search
CPC ................... B01D 2251/304; B01D 2251/402
USPC .......................................................... 435/167
See application file for complete search history.

(56) References Cited

U.S. PATENT DOCUMENTS

| 4,057,401 | A | 11/1977 | Boblitz |
| 4,211,647 | A | 7/1980 | Friedman et al. |
| 4,529,701 | A | 7/1985 | Seely |
| 4,632,758 | A | 12/1986 | Whittle |
| 5,342,524 | A | 8/1994 | Gaddy |
| 6,709,591 | B1 | 3/2004 | Ellis et al. |
| 2002/0079266 | A1 | 6/2002 | Ainsworth et al. |
| 2003/0141244 | A1 | 7/2003 | Hansen et al. |

FOREIGN PATENT DOCUMENTS

| DE | 10119991 A1 | 10/2002 |
| GB | 1462736 A | 1/1977 |
| JP | 11-267450 A | 10/1999 |
| WO | WO 9210270 A1 | 6/1992 |

OTHER PUBLICATIONS

Demirel et al. (Biomass and Bioenergy, vol. 32, p. 203-208, 2008).*
Yokoyama et al. (Applied Microbiology & Biotechnology, vol. 74, p. 474-483, 2007).*
Raposo et al. (Process Biochemistry, vol. 41, No. 6, p. 1444-1450, 2006).*
Mahmoudkhani et al. International Journal of Greenhouse Gas Control, vol. 3, p. 376-384, 2009).*
Mähnert, P.—"Kinetik der Biogasproduktion aus nachwachsenden Rohstoffen und Gülle (Kinetics of fermentation gas production from regenerating raw materials and liquid manure)", 2007, Humboldt University, Berlin (Germany), pp. 21-23; 9 pgs; Includes machine translation in English.
Kaiser, F., et al—"Sicherung der Prozessstabilität in landwirtschaftlichen Biogasanlagen, (Protection of process stability in agricultural biological gas facilities)", 2007, Bayerische Landesanstalt für Landwirtschaft (LfL), Freising (Germany), published by Bavarian National Institute for Agriculture (LfL); pp. 6-14, 29 pgs; Includes machine translation in English.
Raposo, F., et al—"Influence of inoculum to substrate ratio on the biochemical methane potential of maize in batch tests", 2006, Process Biochemistry, vol. 41, Issue No. 6, Elsevier, XP025124807, pp. 1444-1450; 7 pgs.
Kasali, George B., et al—"Sodium Bicarbonate Effects on the Anaerobic Digestion of Refuse", 1989 Journal of Chemical Technology and Biotechnology, vol. 45, Issue No. 4, XP002606832, pp. 279-289; 11 pgs.
Scherer, P.—"Bestimmung der Abbauraten von Biogasanlagen (Determination of the degradation rates of biogas plants)", Hochschule fur Angewandte Wissenschaften (HAW) Hamburg, Brandenburgische Energie Technologlie Initiative (ETI), 2008, HAW Hamburg, Research and Transfer Centre for Renewable Energy and Process efficiency (FTZ REEVE), biogas laboratory, Potsdam, Germany, XP002606833, pp. 1-7, 16 pgs, Includes machine translation in English.
Barber, N.R.—"Lime/ Soda Bicarbonate Treatment Increases Sludge Digester Efficiency", 1978, Journal of Environmental Sciences, vol. 21, Issue No. 2, XP008128116, pp. 28-30; 3 pgs.
Demirel, B., et al—"Production of methane from sugar beet silage without manure addition by a single stage anaerobic digestion process", 2008, Biomass and Bioenergy, vol. 32, Issue No. 3, Elsevier, XP022479372, pp. 203-209, 7 pgs.
Brovko, N., et al—"Optimizing Gas Production, Methane Content, and Buffer Capacity in Digester Operation", 1977, Water & Sewage Works, vol. 124, Issue No. 7, XP008128243, pp. 54-57; 6 pgs.
Ghaly, A E., et al—"Controlling the pH of Acid Cheese Whey in a Two-Stage Anaerobic Digester with Sodium Hydroxide", 1999, Energy Sources, Taylor & Francis Ltd., vol. 21, Issue No. 6, XP008128237, pp. 475-502; 28 pgs.
Florencio, L.—"pH-Stability in Anaerobic Bioreactors Treating Methanolic Wastewaters"; 1996, Water Science and Technology, vol. 33, Issue No. 3, Pergamon, pp. 177-184; 8 pgs.
Ghaly, A.E., et al—"Effect of reseeding and pH control on the performance of a two-stage mesophilic anaerobic digester operating on acid cheese whey", 2000, Canadian Agricultural Engineering vol. 42, Issue No. 4, pp. 173-183; 11 pgs.

(Continued)

Primary Examiner — Susan Hanley
Assistant Examiner — Damon B Bowe
(74) Attorney, Agent, or Firm — Beatrice C. Ortego

(57) ABSTRACT

Process for the production of a biogas containing methane from an organic matter amenable to anaerobic digestion comprising feeding an anaerobic digester with the organic matter, said anaerobic digester containing a digestion medium comprising microorganisms capable of digesting said organic matter, wherein the total inorganic carbon concentration of the digestion medium is maintained above 9000 mg of equivalent $CaCO_3/l$ and the buffering capacity is maintained above 200 mmol/l by the addition of a buffering reagent comprising sodium bicarbonate to the digestion medium.

21 Claims, 5 Drawing Sheets

(56) References Cited

OTHER PUBLICATIONS

Anunputtikul, Wantanee, et al—"Laboratory Scale Experiments for Biogas Production from Cassava Tubers"; 2004, The Joint International Conference on "Sustainable Energy and Environment (SEE)" Dec. 1-3, 2004, Hua Hin, Thailand, pp. 238-243; 6 pgs.

Kumar, A., et al—"Impact of Ni(II), Zn(II) and Cd(II) on biogassification of potato waste", 2006, Journal of Environmental Biology, vol. 27, Issue No. 1, pp. 61-66; 6 pgs.

Leitao, R,C., et al—"The effects of operational and environmental variations on anaerobic wastewater treatment systems: A review", 2006, Bioresource Technology, vol. 97, Issue No. 9, pp. 1105-1118; 14 pgs.

* cited by examiner

PROCESS FOR PRODUCING BIOGAS

CROSS-REFERENCE TO RELATED APPLICATIONS

This application is a U.S. national stage entry under 35 U.S.C. §371 of International Application No. PCT/EP2011/057561 filed May 10, 2011, which claims priority to European application No. 10162425.2 filed on May 10, 2010, the whole content of this application being incorporated herein by reference for all purposes.

This application claims priority to European application No. 10162425.2 filed on May 10, 2010, the whole content of this application being incorporated herein by reference for all purposes.

TECHNICAL FIELD

The invention relates to a process for producing biogas from organic matter in a biogas reactor (called digester in the following).

PRIOR ART

Biogas is the common name of the gas resulting from anaerobic fermentation of organic matter by microorganisms. Biogas is generally composed of methane (50-65 volume %), carbon dioxide (35-45 vol. %), nitrogen (0-3 vol. %), hydrogen (0-1 vol. %) and hydrogen sulphide (0-1 vol. %). Biogas is an alternative energy source which has started to be used in both rural and industrial areas since end of the fifties.

The organic matter is a material comprising carbon that has the property of being decomposed by the action of microorganisms and especially by methanegenic bacteria to produce methane, in a process depending on factors such as temperature, pH, carbon/nitrogen ratio. The organic matter may include agricultural residue, animal residue, industrial residue, food processing residue, urban garbage, and marine algae. Generally in industrial biogas producing units, a mix of cereals silage (such as maize silage), grass silage and animal manure (such as chicken, pig and cow manure) are used.

The biogas production can be divided into four phases. In a first phase, namely the hydrolysis, the complex molecules of the organic matter such as carbohydrates, lipids, and proteins are decomposed into their monomers. Subsequently there is a degradation of monomers into short chains of organic acids such as fatty acids, amino acids, and propionic acid (acidogenesis). In a third step (acetogenesis) and fourth step (methanogenesis), the generation of acetic acid occurs first of all, and following that of methane $CH_4$ and carbon dioxide $CO_2$, generating the biogas.

The production of biogas can be operated at different temperatures for instance between 20 to 70° C. The methanegenic fermentation is a biological process involving many microorganisms which best reproduce at different temperatures: psicrophilics bacteria at about 20° C., mesophilics bacteria at about 35° C., and thermophilics bacteria at about 55° C. Generally industrial biogas digesters are operated at a temperature between 30° to 42° C.

The optimum carbon/nitrogen/phosphorus/sulphur ratio in digesters is about 500/15/5/3 for hydrolysis and acidogenesis phases, and about 600/15/5/3 for acetogenesis and methanogenesis phases.

Methanogene microorganisms belong to the group of Archeabacteria. Several of methanogene microorganisms metabolisms processes use coenzyme factors, such as coenzyme factor F430 with nickel central ion, or such as formyl-ethanofuran-dehydrogenase with molybdenum central ions. Therefore, micronutrients containing nickel, molybdenum but also iron, zinc, cobalt and manganese may be added to the biogas digester when the micronutrients are insufficiently present in the organic matter.

The optimum pH value at the hydrolysis and acidogenesis phases is in the range of pH 3.5 to 6.3. This corresponds to acidic conditions. The optimum pH at the acetonogenesis and methanogenesis phases is in the range of pH 6.6 to 7.8. This corresponds to near neutral pH conditions.

The biogas production is generally operated by batch process or by continuous process. In a batch process, a given quantity of organic matter is introduced in a digester until the chemical and biological reaction reaches the desired advancement degree. In a continuous process the reaction is continuously implemented in a digester, adding continuously or semi continuously the feeding matter into the digester; the products of the reaction (the biogas, and the overflow of the digester content) are recovered continuously or semi-continuously at one or several outlets of the digester at the rate of the desired advancement for the reaction. When a digester is run continuously, the feeding is implemented generally semi continuously. In this later case the feeding of the digester is implemented by portions of the daily, or weekly needs.

The biogas production is generally operated in one stage units wherein the four phases of the digestion (hydrolysis, acidogenesis, acetogenesis, methanogenesis) are carried out in the same digester. The biogas production can also be carried-out in two stages units: the first two phases in acidic conditions are operated in a separated hydrolyser-reactor feeding a second reactor, namely the anaerobic digester, wherein the last two phases are carried out in near neutral conditions.

GB 1462736 describes an anaerobic biological treatment of waste waters in which a portion of the effluent is recycled to the inlet of the anaerobic digester to control its pH with an optional addition of a pH buffering reagent such as calcium carbonate or sodium bicarbonate but the document is silent on the total inorganic carbon content and buffering capacity of the digester; moreover the organic feeding load of the digester is very low.

U.S. Pat. No. 4,529,701 describes a process for enhancing bacterial action in an anaerobic digester using a pyrophosphate stimulating product with sodium bicarbonate to regulate the pH, but the total inorganic carbon and the organic feeding load of the digester are low also.

Biogas digesters, containing living microorganisms, are very sensitive to operating conditions. When there is an excessive addition of acidifying organic matter as cereals or grass silage, or an overfeeding of the digester, or when there is a fast change of the quality of the organic matter, then methane production falls. This can lead also to a digester upset stopping totally methane production. It this later case a complete shutdown of the digester is necessary with the withdrawal of the digestion medium. A restart of a digester takes commonly 50 days, and up to several months to recover completely the biogas production level, impacting correspondingly the stream factor of the biogas unit and reducing the annual biogas production.

One known factor to follow up for the good working of an anaerobic digester is the buffering capacity ($KS_{4.3}$) of the digestion medium to be maintained in the 250 to 500 mmol/l (Bavarian national Institute for agriculture LfL—Information leaflet: protection of process stability in agricultural biological gas facilities—July 2007).

One other known factor to follow up for the good working of an anaerobic digester is the volatile organic acids (such as formic acid, acetic acid, propionic acid, butyric acid) of the clear liquid of the digester. The measure can be made according to the German standard DIN 38414-19 (Determination of the steam-volatile organic acids S19—December 1999). Other authors also use the titration standard method from VTI (Thüringer Verfahrenstechnisches Instituts für Umwelt und Energie—Arbeitsanweisung zur Bestimmung des Verhältnisses FOS/TAC) to measure a titration volatile organic acids (in German language "Flüchtige organische Säuren" or FOS value) and report that the ratio of the volatile organic acids, expressed in FOS value in mg equivalent acetic acid (HAc) per liter, reported to the inorganic carbon content of the clear liquid expressed in mg of equivalent $CaCO_3$ per liter (in German language "Totales anorganisches Carbonat" or TAC), has to be maintained below 0.8 or according to different authors below 0.6, and higher than 0.1. Though it has been demonstrated (Mähnert P. "Kinetics of digestion gas production", thesis at the Humboldt University, Berlin, March 2007) that a high volatile organic content is the result of an insufficient anaerobic digestion, and it is not the cause.

The best practices of existing biogas units, such as the ones published by the Bavarian national Institute for agriculture LfL (F. Kaiser et al., Information leaflet of Bayerische Landesanstalt für Landwirtschaft: protection of process stability in agricultural biological gas facilities—July 2007) teach a maximum organic matter feeding rate of:
  2 to 3 kg of dry matter per cubic meter of digester and per day when fed with cereal silage and grass silage (NawaRo: "Nachwachsender Rohstoff") without animal manure and,
  3 to 4 kg of dry matter per cubic meter of digester and per day when fed with cereal silage and grass silage (NawaRo: "Nachwachsender Rohstoff") with animal manure.

Therefore there is a need to improve the anaerobic processes for biogas production enhancing biogas quality and to improve the anaerobic digestion productivity of the anaerobic digesters.

SUMMARY OF THE INVENTION

The invention relates to a process for improving the production of a biogas containing methane from an organic matter amenable to anaerobic digestion comprising feeding an anaerobic digester with the organic matter, said anaerobic digester containing a digestion medium comprising microorganisms capable of digesting said organic matter, wherein:
  the total inorganic carbon concentration of the liquid of the digestion medium is maintained above 9000 mg of equivalent $CaCO_3$/l and,
  the buffering capacity of the digestion medium is maintained above 200 mmol/l,
by the addition of a buffering reagent comprising sodium bicarbonate to the digestion medium.

It is another object of the present invention to reduce the amount of hydrogen sulphide of the generated biogas using sodium bicarbonate.

It is a further object of the present invention to provide an improved process for biogas production using additives comprising bone char.

DETAILED DESCRIPTION OF THE INVENTION

Figure 1:
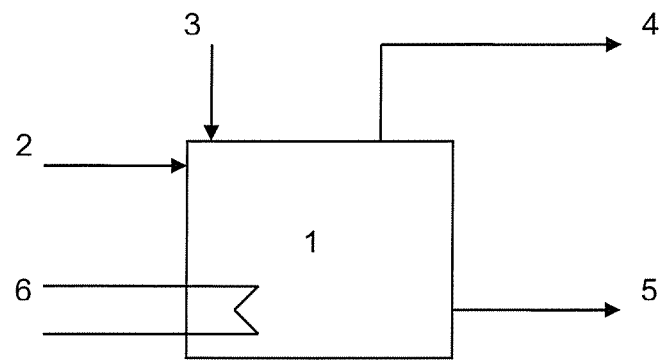
FIG. 1 is a schematic illustration of an embodiment of the process run in one digester (one stage process) in accordance with the principles of the present invention.

One of the objects of the invention is to improve the productivity of biogas digesters enabling feeding rates above the commonly best practices ones.

It has been surprisingly noticed that a biogas digester can be operated with a higher feeding rate than the present maximum best practices ones, and on a long period of time, with a higher methane content of the biogas, a lower "rest gas potential" of the organic matter residues at the output of digester, a higher yield in organic to methane transformation, a reduced amount of hydrogen sulphide of the biogas, and without acidosis incidents when the digester is operated concomitantly with a total inorganic carbon concentration above 9000 mg of equivalent $CaCO_3$/l and a buffering capacity above 200 mmol/l, thanks to the addition of buffering reagent comprising sodium bicarbonate.

Consequently the invention relates to a process for the production of a biogas containing methane from an organic matter amenable to anaerobic digestion comprising feeding an anaerobic digester with the organic matter, said anaerobic digester containing an aqueous medium comprising microorganisms capable of digesting said organic matter,
wherein:
  the total inorganic carbon concentration of the aqueous liquid of the digestion medium is maintained above 9000 mg of equivalent $CaCO_3$/l and,
  the buffering capacity is maintained above 200 mmol/l,
by the addition of a buffering reagent comprising sodium bicarbonate to the digestion medium.

In the present invention, the total inorganic carbon concentration of aqueous liquid of the digestion medium is maintained above 9 000, preferably above 9500, more preferably above 10 000, even more preferably above 10500, and most preferably above 15 000 mg of equivalent $CaCO_3$/l. Concomitantly, the buffering capacity of the digestion medium is maintained above 200, preferably above 210, more preferably above 220, even more preferably above 230, and most preferably above 250 mmol/l. Excessive values of buffering capacities are not necessary and induce higher cost of buffering reagent. Therefore, the buffering capacity of the digestion medium is preferably at most 500, more preferably at most 400 mmol/l The term total inorganic carbon concentration is understood to mean the concentration of carbon not in an organic form, of the aqueous liquid of the digestion medium. The inorganic carbon species include carbon dioxide, carbonic acid, bicarbonate anion, and carbonate anion. In the present document, the inorganic carbon concentrations of the aqueous liquid of the digestion medium are measured according to the analytical method described in example 1. It is expressed as mg of equivalent $CaCO_3$ per liter of the aqueous liquid.

The team buffering capacity is understood to mean the total alkalinity of the digestion medium, including the solid matters in suspension, when measured with diluted strong acid HCl 0.1 N down to pH 4.3: in the present document, the buffering capacity of the digestion medium is measured according to DIN 38409-7 standard (German standard method for the examination of water, waste water, and sludge of acid and bas capacity—March 2004) related to the determination of the $K_{S4.3}$ value (or in German: "Säurekapazität bis zum pH-wert 4.3"), with the only differences that the digestion medium as such, including the solid matters in suspension, is used for the measurement, and that hydrochloric acid (HCl) is used as strong acid rather than hydrosulfuric acid ($H_2SO_4$). It is expressed as milli moles of alkalinity per liter of digestion medium (mmol/l).

The teen buffering reagent is understood to mean a reagent that when added in sufficient quantity to the digestion medium acts on the pH value to either decrease the pH or increase it to a desired value, and having the property to limit pH variations when a strong acid or strong base is added to the digestion medium. Generally a buffering reagent consists of a mixture of a weak acid and its conjugate base or a weak base and its conjugate acid.

In the present invention the buffering reagent comprising sodium bicarbonate may be a buffering reagent comprising sodium bicarbonate ($NaHCO_3$) in the strict sense. In this description it also covers buffering reagents comprising compound salts including sodium bicarbonate such as: sodium sesquicarbonates ($NaHCO_3.Na2CO_3.2H_2O$), wegscheiderite salt ($Na2CO_3,3NaHCO_3$), or mineral ores such as nahcolite ($NaHCO_3$) or trona ($NaHCO_3.Na2CO_3.2H_2O$). Buffering reagents comprising sodium bicarbonate in the strict sense are recommended.

In an advantageous embodiment of the invention, the feeding rate of the anaerobic digester with the organic matter is at least 4, or at least 4.1, or at least 4.3, or at least 4.5, or at least, 4.7, or at least 4.9, or at least 5.0, or at least 5.2, or at least 5.4, or at least 5.6, or at least 5.8 kg, or at least 6 kg of dry organic matter per cubic meter of digestion medium and per day; the feeding rate is preferably at least 4.1, more preferably at least 4.5, and most preferably at least 5 kg of dry organic matter per cubic meter of digestion medium and per day.

In a preferred embodiment of the present invention, the feeding rates of the organic matter of the above advantageous embodiment are maintained at least 2 days, preferably at least one week, and more preferably at least one month. This enables to increase sensitively the productivity of the anaerobic digester.

In an advantageous embodiment of the present invention, the anaerobic digester is operated continuously. In a preferred embodiment the anaerobic digester is operated continuously and the feeding rate of the anaerobic digester with the organic matter is at least 4, preferably at least 4.1, more preferably at least 4.5, and most preferably at least 5 kg of dry organic matter per cubic meter of digestion medium and per day. When the anaerobic digester is operated continuously, the hydraulic residence time, defined as the total useful volume of aqueous medium of the digester divided by the aqueous medium outflow of the digester is generally at least 10 days, advantageously at least 20 days, more advantageously at least 30 days. The hydraulic residence time is generally at most 250 days, advantageously at most 120 days, more advantageously at most 90 days.

In the present invention, the buffering reagent comprising sodium bicarbonate comprises at least 30%, preferably 50%, more preferably 70%, and most preferably 90% in weight of sodium bicarbonate.

The buffering reagent comprising sodium bicarbonate may be added in liquid solution, in liquid suspension or in solid form such as a powder.

In an advantageous embodiment the sodium bicarbonate of the buffering reagent comprising sodium bicarbonate, is a powder that has a particle size distribution such that at least 10%, preferably 30%, more preferably 50% of the particles have a diameter of more than 100 μm.

The anaerobic digester may be fed with an organic matter selected from: sugar and starch containing plants, oil and protein containing plants, cereals grains, cereals plants, cereals silage, cereal straw, leaves, wood, grass silage, sugar beet, sugar beet pulp, beet leaf silage, sugarcane, sugarcane bagasse, clover grass mixtures, alfalfa, sorghum, sunflower, sunflower silage, cotton silage, rapeseed, rapeseed wastes, sunflower, sunflower wastes, soybean, soybean wastes, oilpalm, oil palm wastes, bean, bean wastes, bioethanol process residues, bioethanol process waste waters, transesterification wastes, transesterification wastes waters, animal residues, agro and organic industrial residues, food industry residues, urban organic garbage, urban waste waters and combinations thereof. Advantageously, animal residues are chosen among cow cattle, swine, sheep, goats, poultry, camel, alpaca, dromedary, llama, equidae manure and combinations thereof. Generally the organic matter is selected from vegetal or animal origins or combinations thereof. Advantageously the anaerobic digester is fed with a mix of cereals silage, grass silage and animal manure. Mixture of maize silage, grass silage, pig manure and/or cow manure is particularly advantageous.

Typical values of composition of usable organic matter such as cereals silage, grass silage, maize silage for present invention are listed in Thüringer Landesanstalt für Landwirschaft publication—Langzeituntersuchungen zur Qualität der in der Thüringer Tierproduktion eingesetzten Futtermittel-Ergebnisse Silagemonitoring—Ewischenbericht 2008—Themen Nr 46.08.260 von Thüringer Ministerium für Landwirschaft und Naturschutz—E. Herzog—in Tables 3, 7, 11 which are incorporated herewith by reference.

Generally values of composition of usable organic matter such as animal manure are: 6 to 12 w % of dry matter content (TS), and 75 to 85% of organic content reported to the dry matter (oTS). Those values are measured according German standards DIN EN 12880 and 12879.

In an advantageous embodiment of present invention both organic matters from plants and from animal manure is used for feeding the digester. In that case, the raw weight ratio of animal manure to plant matter is at least 0.3, preferably at least 0.35 t/t. Generally the raw weight ratio of animal manure to plant matter is at most 10, preferably at most 4, more preferably at most 3 t/t.

In one embodiment of the invention, addressing mesophilic microorganisms system, the digestion medium temperature in the digester is advantageously at least 30°, advantageously at least 33°, preferably at least 35°, more preferably at least 36, most preferably at least 37° C. The temperature is advantageously at most 45° C., preferably at most 42° C.

In another embodiment of the invention, addressing thermophilic microorganisms system, the digestion medium temperature in the digester is advantageously at least 45° C., preferably at least 50° C. The temperature is generally at most 60° C., preferably at most 57° C.

The temperature of the digester may be regulated by any known means in the art: such as for instance heating/cooling part on the digestion medium by an external or an internal heating/cooling loop. Heating/cooling calories may be provided by solar heating, recovery of the low temperature biogas combustion exhaust gas, hydrothermal heating, heat pump, recovery of heat stored during summer time in thermal capacities and recoverable during winter time.

The anaerobic digester may be of mixed tank reactor type or of up-flow anaerobic sludge blanket (UASB) type. In present invention, the anaerobic digester is preferably of a mixed tank reactor type. In that case the anaerobic digester is advantageously equipped with an agitation device in order to homogenize the digestion medium, promote an effective digestion and decrease the foam or crust formations. A periodical agitation, for instance 10 minutes every three hours, or 5 minutes every hour, is preferred.

In an embodiment of the present invention, the process is run in one digester. This corresponds to a one stage unit process. In this embodiment, the four phases (hydrolysis to methanogenesis phases) of the biogas production may take place in the same digester. FIG. 1 is an illustration of such embodiment using one digester 1. The organic matter 2 amenable to anaerobic digestion is fed in the anaerobic digester 1 containing an aqueous medium comprising microorganisms capable of digesting said organic matter, wherein the total inorganic carbon concentration is maintained above 9000 mg of equivalent $CaCO_3$/l and the buffering capacity is maintained above 200 mmol/l by the addition of a buffering reagent 3 comprising sodium bicarbonate. A heating or cooling equipment is used to control the digester temperature with a heating or cooling fluid 6. The produced biogas 4 is withdrawn from the digester 1 for further use. And the digestion medium partially exhausted 5 is withdrawn from digester.

In an advantageous embodiment of the present invention several anaerobic digesters are operated in series or in parallel.

In a preferred embodiment at least two reactors are operated in series. In this preferred embodiment, the first reactor(s) is (are) run at acidic pH and the subsequent reactor(s) is (are) run at near neutral pH. To differentiate those two kinds of reactors in the present description, the reactors run at acidic pH conditions are called hydrolyser-reactors, and reactors run at near neutral conditions are called digesters. In this embodiment of the present invention, the process relates to the digester(s). That is to say, that the addition of the buffering reagent comprising sodium bicarbonate is done in the digester(s). In this preferred embodiment, the organic matter amenable to anaerobic digestion is withdrawn from at least one hydrolyser-reactor. As such, a raw organic matter feeds one or several hydrolyser-reactor(s). The hydrolyser-reactor is generally operated in present invention at acidic pH between 3.8 and 5.8, at a temperature of 40 to 55° C., with a hydraulic residence time between 3 to 11 days, at a feeding rate of 5 to 20 kg of dry organic matter per cubic meter of hydrolyser-reactor medium and per day. In the hydrolyser-reactor(s) most part of hydrolysis and acidogenesis phases are operated. Then the content of the hydrolyser-reactor(s) is partly withdrawn to feed subsequent anaerobic digester(s) producing biogas. In the anaerobic digester(s) most part of the acetogenesis and methanogenesis phases are operated.

This configuration in which spatial and temporal separations may be made between part of hydrolysis and acidogenesis phases, and part of acetogenesis and methanogenesis phases, enables to improve the control of acidic and near neutral phases operations and to increase biogas production. For instance different temperatures can be operated in the different reactors according the phases to privilege: up to 70° C. for the acidic hydrolysis and acidogenesis phases, up to 56° C. for the acetogenesis phase, up to 70° C. for the methanogenesis phase. Also different hydraulic residence time can be adapted to the different phases taking place in the reactors.

Figure 2:
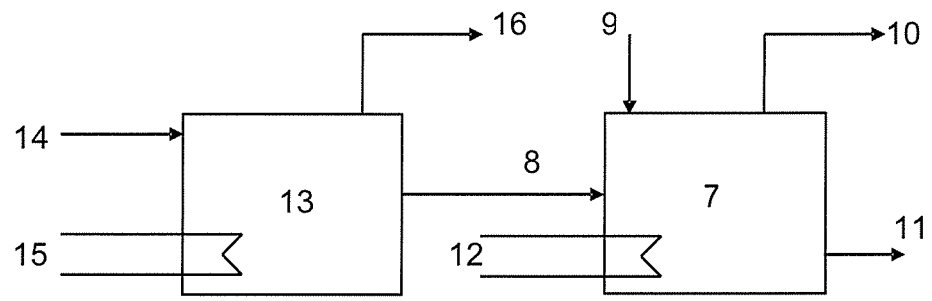
FIG. 2 is a schematic illustration of a preferred embodiment of the process run in two reactors (two stages process) in accordance with the principles of the present invention.

FIG. 2 is an illustration of such preferred embodiment, using two reactors 7 and 13, illustrating a two stages unit. A raw organic matter 14 feeds a hydrolyser-reactor 13 run in acidic conditions. A heating or cooling equipment is used to control the hydrolyser-reactor 13 temperature with a cooling or heating fluid 15. Part of the resulting content of the hydrolyser-reactor 13 is withdrawn and introduced as feeding organic matter 8 in the subsequent digester 7. Wherein the total inorganic carbon concentration is maintained above 9000 mg of equivalent $CaCO_3$/l and the buffering capacity is maintained above 200 mmol/l by the addition of a buffering reagent 9 comprising sodium bicarbonate. A heating or cooling equipment is used to control the digester 7 temperature with a heating or cooling fluid 12. The produced biogas 10 is withdrawn from the digester 7 for further processing and use. The produced gas 16 in the hydrolyser-reactor 13 is removed for further specific processing or optional mixing with the produced biogas 10. The partially exhausted digestion medium 11 is withdrawn from digester 7.

In an advantageous embodiment of this preferred embodiment, part of the partially exhausted digestion medium withdrawn from digester, is recycled back as feeding substrate of the hydrolyser-reactor with the feeding matter.

The total inorganic carbon of the aqueous liquid of the digestion medium and the buffering capacity of the digestion medium of the digester may be checked periodically: several times a day, performed for instance with an automatic sampler and analyzer, or checked once per day, or once every few days, performed for instance manually. Advantageously those two parameters should be checked at least once a week, and preferably the buffering reagent comprising sodium bicarbonate is added at least once a day.

Advantageously the amount of the buffering reagent comprising sodium bicarbonate added in the digester calculated on a daily base is at least 0.05 weight percent (w %), preferably at least 0.10 w %, more preferably at least 0.12 w % of the dry matter content of the digestion medium. The amount of the buffering reagent calculated on a daily base is understood to mean the amount of buffering reagent added in the digester divided by the time period expressed in days between two additions of the buffering reagent. In the case there is a continuous or semi-continuous addition of the buffering reagent, the amount of the reagent calculated on a daily base will be the quantity of the buffering reagent added in one day period.

In an advantageous embodiment of the invention the volatile organic acids content of the aqueous liquid of the digestion medium is maintained to less than 3000, preferably less than 1500 mg HAc/l, with the addition of a buffering reagent comprising sodium bicarbonate. The volatile organic acid is measured according the analytical method described in example 1. It is expressed as milligram of equivalent acetic acid (HAc) per liter (L).

In the event that the total inorganic carbon concentration of the digestion medium falls to less 9000 mg of equivalent $CaCO_3$/l and that concomitantly the volatile organic acids goes up to more than 3 000 mg HAc/l, a buffering reagent comprising sodium bicarbonate is added to the digestion medium to increase the total inorganic carbon concentration of the digestion medium above 9000 mg equivalent $CaCO_3$/l.

If too important quantities of sodium based buffering reagent are introduced into the digester, the microorganisms of the biomass may be stressed or even totally killed when the salinity is too high. Therefore the addition of the buffering reagent comprising sodium bicarbonate is limited such as the sodium concentration of the aqueous liquid of the digestion medium is less than 60 g/l, preferably less than 15 g/l, most preferably less than 6 g/l.

Though to be efficiently buffered with a reagent containing sodium bicarbonate, the sodium concentration of the digestion medium is at least 0.6, preferably at least 0.9, more preferably at least 1.5 and most preferably at least 2 g/l.

The pH value of the aqueous liquid of the digestion medium is an important parameter for a correct biogas production. A pH value too low in the biogas digester is improper to operate correctly biogas fermentation. The pH value may be advantageously measured according DIN 38404-5 German standard method (August 2005) of determination pH values of water, waste-water, and sludge. Advantageously the pH value of the aqueous liquid of the digestion medium in present invention is at least 6.80, preferably at least 6.90, more preferably at least 7.35. A too high pH is also detrimental. The pH value in present invention is advantageously at most 7.90, preferably at most 7.80, and more preferably at most 7.75.

A correct pH value is important to have a good transformation yield of organic matter into biogas, but the pH value taken alone is insufficient to operate and to control a biogas digester. This is particularly the case at high feeding rate. Indeed it has been observed that, even at a good pH value, when there is an excessive addition of organic matter or when there is a fast change of the quality of the organic matter, the pH value begins to fall, impairing the subsequent methane production. When the pH value drop is observed, it is too late to add even fast reacting buffering reagent to correct the situation and avoid the shock to microorganisms: methane production falls rapidly. Therefore the information given by the pH value alone does not prevent the partial or total failure of the digester leading to the decrease of the production of biogas. Oppositely in present invention a sufficient total inorganic carbon concentration of the aqueous liquid combined with a sufficient buffering capacity of the digestion medium brought by a buffering reagent comprising sodium bicarbonate enables a high feeding rate of the biogas digester without most of commonly observed digestion shocks or failures.

In a particular embodiment of the invention, in the event that the pH-value of the aqueous liquid of the digestion medium falls below 6.5, a buffering reagent comprising calcium carbonate, and/or magnesium carbonate, and/or sodium carbonate, is introduced into the digestion medium to increase the pH-value up to at least 6.0, preferably up to at least 6.5, and then a buffering reagent comprising sodium bicarbonate is introduced into the digestion medium to increase the pH-value up to at least 6.6, preferably to at least 6.9, more preferably up to at least 7.35. This increase of the pH value in two steps enables to limit the consumptions of the buffering reagent comprising sodium bicarbonate with lower cost reagents comprising calcium and/or magnesium carbonate, and/or sodium carbonate. Indeed sodium bicarbonate has shown particularly effective to increase the total inorganic carbon concentration of the aqueous liquid of the digestion medium and the buffering capacity of the digestion medium above pH 6.5, as calcium and/or magnesium carbonate are not. Below pH value of 6.5, or 6.0, calcium and/or magnesium sufficiently react with the digestion medium to increase the pH at least at 6.5.

Buffering reagents comprising sodium carbonate are effective for increasing the pH whatever it is below pH value 8.3, though buffering reagents comprising sodium bicarbonate are preferred above pH value of 6.5 as the increase of pH is smoother and avoid excessive alkalinity detrimental to methanogene microorganisms.

In a particular embodiment of the invention, a nutrient additive is introduced into the digestion medium. This is particularly useful when the demanded productivity of the anaerobic digester is high with a high feeding rate of the anaerobic digester. The nutrient additive may be selected from natural or synthetic fertilizing reagents known in the art when the organic matter does not bring an efficient carbon/nitrogen/phosphorus/sulphur ratio to the digester medium. The nutrient additive may also comprises micronutrients selected from: iron, zinc, nickel, molybdenum, cobalt, manganese, selenium, boron, vanadium, titanium, tungsten, arsenic and combinations thereof.

In an advantageous embodiment of the invention, the nutrient additive is selected among calcium phosphate, calcium apatite, sodium phosphate, phosphorus oxide, pyrophosphate, bone char and their combinations.

In a preferred embodiment of the invention, the nutrient additive comprises bone char. Bone char is a granular material made by charring animal bones at high temperatures in an oxygen-depleted atmosphere. Bone char comprises calcium phosphates, carbon and micronutrients. It has been observed that the addition of bone char to the digestion medium according the present invention, increases biogas production reported to the dry organic matter, and improves the methane content of biogas. Without wishing to be bound by a theoretical explanation and without excluding other modes of action, the inventors think that the bone char added to the digestion medium, is slowly solubilized and nutrients and micronutrients can be usefully metabolized by the microorganisms of the digestion medium. Moreover bone char presenting a large specific surface area may also adsorb and removes specific substances or elements in the digestion medium that are detrimental when present in excess.

Amounts of nutrient additives to be selectively added to the digestion medium can be calculated in order to obtain nutrients ratio close to optimal ratios or close to optimal values known in the art. Advantageous phosphorus or sulphur to carbon and nitrogen ratios are given at the beginning of this description. When the dry matter content of the digestion medium is between 3 to 9 weight percents, advantageous concentrations of micronutrients in the digestion medium are: Iron (Fe): 37 to 250 mg/kg; Nickel (Ni): 0.2 to 1.5 mg/kg; Cobalt (Co): 0.02 to 0.5 mg/kg; Copper (Cu): 0.5 to 4.0 mg/kg; Manganese (Mn): 5 to 75 mg/kg; Molybdenum (Mo): 0.0025 to 0.8 mg/kg; Selenium (Se): 0.0025 to 0.2 mg/kg; Tungsten (W): 0.005 to 1.5 mg/kg; Zinc (Zn): 1.5 to 20 mg/kg. In those ranges of advantageous concentrations, the optimal values of micronutrients concentrations are: Iron (Fe): 120 mg/kg; Nickel (Ni): 0.8 mg/kg; Cobalt (Co): 0.09 mg/kg; Copper (Cu): 2.0 mg/kg; Manganese (Mn): 15 mg/kg; Molybdenum (Mo): 0.2 mg/kg; Selenium (Se): 0.025 mg/kg; Tungsten (W): 0.03 mg/kg; Zinc (Zn): 10 mg/kg.

In a variant of the present invention, the process further comprises the steps of:
  collecting the biogas containing methane,
  burning the biogas with a gas containing oxygen into an exhaust gas containing acidic gas matter,
  injecting sodium bicarbonate solid particles in the exhaust gas,
  carrying out a neutralization of part of the acidic gas matter of the exhaust gas into corresponding sodium salts and a partially purified exhaust gas.

Those acidic gases may be acidic compounds such as: sulphur dioxide, sulphur trioxide, selenium oxides, nitrogen oxides (NOx), or halogenated acids (HX). Indeed sodium bicarbonate has shown to be an efficient reagent to absorb mineral and organic acidic gases at temperatures above 130°

C. In an advantageous embodiment of the variant of the present invention, the sodium bicarbonate particles, injected in the exhaust gas, have a particle size distribution such that at least 50 weight %, of the particles have a diameter of less than 40 µm, preferably less than 30 µm, more preferably less than 20 µm. In a preferred embodiment of the variant of the present invention, neutralization of part of the acidic gas matter is carried out at a temperature of at least 130° C., preferably at least 140° C., more preferably at least 150° C. In a more preferred embodiment of the variant of the present invention, neutralization of part of the acidic gas matter is carried out at a temperature of at most 400° C., preferably at most 300° C., more preferably at most 250° C., most preferred at most 220° C.

Carrying out the neutralization of the acidic gas matter at those temperatures, enables to transform part of sodium bicarbonate into sodium salt such as sodium sulphite, sodium sulphate, sodium halogenated salts, sodium nitrates. The unreacted sodium bicarbonate is in sodium bicarbonate form or in sodium carbonate form when calcined according the residence time of sodium bicarbonate within the exhaust gas.

In a preferred embodiment, the process of the variant of the present invention additionally comprises the step of:
  collecting the sodium salts from the partially purified exhaust gas,
wherein part of the collected sodium salts is further used as a buffering reagent comprising sodium bicarbonate or used as a buffering reagent comprising calcium carbonate, and/or magnesium carbonate, and/or sodium carbonate added to the digestion medium.

Indeed using part of the collected sodium salts as a buffering reagent comprising sodium bicarbonate or as a buffering reagent comprising sodium carbonate enables to recycle useful salts to the digestion medium such as sulphate, nitrate, or selenite to carry out efficiently the digestion.

An other object of the invention is to improve the quality of the produced biogas: it has been observed that maintaining a sufficient total inorganic carbon concentration of the aqueous liquid of the digestion medium and a buffering capacity of the digestion medium by the addition of a buffering reagent comprising sodium bicarbonate leads to a decrease of hydrogen sulphide of the produced biogas. This is an advantageous improvement of the purity of the biogas, as hydrogen sulphide has to be removed from the biogas before its burning. Indeed hydrogen sulphide leads to corrosion of the burners and exhaust gas parts such as combined power turbines for electricity production and exhaust gas conducts.

Therefore the invention relates also to the use of sodium bicarbonate in the process of present invention to reduce the hydrogen sulphide content in the biogas.

The following examples serve to illustrate the invention in a non-limiting manner, the results of which appear in the tables below.

Example 1

The process according the present invention has been applied in this example in single stage mesophile anaerobic digesters. Three identical digesters were used and were operated on a quasi-continuous mode: the digesters were fed with the organic matter once daily, and run on a five months period. The first digester, referenced KF1, was used as control digester and no buffering reagent containing sodium bicarbonate was added to. The two others digesters, referenced VF2 and VF3, were run according the present invention.

The three anaerobic digesters were made of transparent double-walled acrylic polymer (internal diameter 220 mm and height 305 mm), having a working volume of 10.5 liters. Each digester was equipped with a computer-controlled drive anchor agitator (height 280 mm, broadness 210 mm of the anchor element, rotating speed 50 rpm, duration 2 minutes every hours). The periodical agitation was sufficient to periodically homogenize the digestion medium content and surface.

The organic matter addition and the gas release were made through gas-proof openings in the cover of each digester. Each digester was also equipped with a gas meter, TG05/5 from Ritter Company, filled with a sealing fluid Ondina 909 having a lower evaporation rate than water, to measure the cumulative gas production. Each of the gas meters were equipped with two temperature digital sensors W180 from Convar GmbH Company, for gas and room temperature measures to standardize the gas flow rate whatever the temperature of the gas.

The temperature of the digestion medium and produced biogas was registered on a continuous basis by temperature sensors and the mean of an acquisition computer, and each digester was controlled to a digestion medium temperature of 37.5+/−0.5° C.

Each digester was equipped with an aluminum-coated polyethylene gas bag of 100 liters useful capacity, from Tessrau Company. The composition of the generated biogas for each digester, caught in the corresponding gas bag between two measurements, was analyzed once per day, regarding methane, carbon dioxide, oxygen and hydrogen sulfide content on a calibrated multi gas analyzer: Biogas Monitor BM 2000 from Asynco GmbH Company. The reported measures of the biogas content in the gas bag was done on a basis of the mean value during one hour measurement during the pumping-out of the content of the gas bag. Measurement principles of the multi gas analyzer are: infrared spectrometry for $CH_4$ (range: 0-100 vol. %), $CO_2$ (range: 0-100 vol. %), and electrochemical cell for $O_2$ (0-25 vol. %) and $H_2S$ (0-5000 ppm vol.). The content of each gas bag was completely withdrawn after each daily measure.

The volume and gas composition enabled also to estimate the remaining gas potential of the digestion medium.

The organic matter used for feeding the anaerobic digesters was a standard mixture of cow and pig manure/maize silage/grass silage ("triticale"), used in the corresponding proportions: 550 mL cow and pig manure/1 kg maize silage/230 g grass silage ("triticale"). The corresponding characteristic of each component of the organic matter mixture is given in table 1.

TABLE 1

Composition of the components of the organic matter mixture

| Characteristics | Unit | Cow and Pig used manure | Maize silage | Grass silage "Triticale" |
|---|---|---|---|---|
| pH-value | — | 7.46 | 4.15 | — |
| Dry matter content (TS) | % FM | 7.13 | 31.58 | 90.47 |
| organic content of the Dry matter (oTS) | % TS | 76.87 | 96.4 | 98.5 |
| organic content of the dry matter (oTS) | $g \cdot kg^{-1}$ FM | 54.83 | 294.6 | 852.0 |
| Volatile organic acids (Sr) in $g \cdot kg^{-1}$ of fresh mass | $g \cdot kg^{-1}$ FM | 5.77 | 1.16 | — |

TABLE 1-continued

Composition of the components of the organic matter mixture

| Characteristics | Unit | Components of the feeding organic matter | | |
|---|---|---|---|---|
| | | Cow and Pig used manure | Maize silage | Grass silage "Triticale" |
| Organic content (oS) expressed in g · kg$^{-1}$ of fresh mass of organic matter | g · kg$^{-1}$ FM | 60.6 | 295.8 | 852.0 |
| Organic content (oS) | % FM | 6.1 | 29.6 | 85.2 |

The dry matter content (TS), and the organic content of the dry matter (oTS) were measured according German standards DIN EN 12880 and 12879, describing the measurement at 105° C. of the dry matter content (TS or "Trockensubstanzgehalt"), and the measurement of the organic dry matter after removal of ashes of the matter burned at 550° C. (oTS or "organischer Trockensubstanz").

The fresh mass (FM or "Frischmasse" in German language) corresponds to the mass of the raw material used as organic matter. The fresh mass includes the dry matter, the water, and the volatile compounds.

The volatile organic acids (Sr or "organischen Säuren") of the organic matter were measured according standard DIN EN 38414-19 (German standard method for the examination of water, waste-water and sludge, Sludge and sediments (group S), Part 19: Determination of the steam-volatile organic acid (S 19), December 1999).

The organic content (oS or "organischer Substanz") of the organic matter is calculated as the sum of the organic content of the dry content (oTS) and the volatile organic acids (Sr):

$$g\ oS/kg\ FM = g\ oTS/kg\ FM + g\ Sr/kg\ FM$$

That is to say that organic content (oS) is superior or equal to the organic content of the dry matter (oTS) of the organic matter.

In this example the three digesters were fed on a starting period of 28 days. The three digesters were filled initially with digestion medium coming from a biogas production unit using maize silage, grass silage, and pig and/or cow manure. The same amount and same composition of organic matter were used for feeding the three digesters, fed in once time on a daily basis. The daily feeding rate was remained constant on a week basis, i.e. same amount each day on a 7 days period.

After the starting period of 28 days (4 weeks), the organic content (oS) feeding rate was progressively increased from 1 gram of organic content (oS) per liter of digestion medium and per day (equivalent to kg/m$^3$/day) to reach 3.5 gram of organic content per liter and day (kg/m$^3$/day) for each anaerobic digester of working volume 10.5 L.

Then the three digesters were fed above 4.0 gram of organic content per liter and day (equivalent to kg/m$^3$/day): from 4.09 up to 6.01 kg/m$^3$/day during 5 weeks (35 days). That is to say above maximum feeding rates of the art.

In a third period the feeding rate was decreased to 2.54 kg/m$^3$/day and re-increased rapidly to 5.52 kg/m$^3$/day to simulate variations of the feeding rates.

The first digester, hereafter referenced KF1 ("Kontrollfermenter 1") was used as control digester without sodium bicarbonate addition.

In the two other digesters, hereafter referenced VF 2 and VF 3 ("Versuchsfermenter 2 & 3"), sodium bicarbonate BICAR Tec from the Solvay Chemicals company was used as a buffering reagent to maintain a total inorganic carbon concentration of the aqueous liquid of the digestion medium during the anaerobic digestion above 9000 equivalent CaCO$_3$ mg/l and a buffering capacity of the digestion medium above 200 mmol/l.

The quantities of sodium bicarbonate added to digesters 2 and 3 started from day 77 when the feeding rate of the organic matter started to became high (higher than 3.0 kg/m$^3$/day). Daily amounts of sodium bicarbonate where from 0.5 w % (weight percent), up to 1.0 w.% and down to 0.125 w. % of the dry matter (TS) of the digestion medium.

The pH value was measured according DIN38404-5 German standard method (August 2005) of determination pH values of sludges.

The total inorganic carbon (TAC value) and volatile organic acids value (FOS value) of the liquid of the digestion medium was measured as follow:
- 50 mL of representative digestion medium is sampled from the anaerobic digester
- the sample is filtered on lab fast filtering paper, or alternatively centrifuged the sample at 4500 rpm for 20 minutes at 10° C. to obtain a clear liquid
- 20 mL (exact $V_0$ mL) of the clear liquid is withdrawn with a pipette, and added in a beaker stirred with a magnetic agitator and equipped with a pH probe. Distilled water is added to beaker, if needed, such as the pH probe be in contact with the solution. The magnet agitator is switched on during the titration to homogenize permanently the liquid
- the liquid is titrated with 0.1 N H$_2$SO$_4$ to pH 5; and the volume of acid used $V_1$ mL is noted
- the liquid is then titrated with 0.1 N H$_2$SO$_4$ to pH 4.4; and the volume of acid used (from pH 5.0 to pH 4.4): $V_2$ mL is noted.

If $V_0$ is the actual originally sampled when deviating from 20 mL, the calculation formula of the TAC and empirical FOS values are:

Total inorganic carbon (TAC) is:

$$TAC(\text{mg of equivalent CaCO}_3/L) = 20\ mL/V0(mL) \times V1(mL) \times 250$$

Volatile organic acids (FOS) is:

$$FOS(\text{mg HAc/l}) = (20\ mL/V0(mL) \times V2(mL) \times 1.66 - 0.15) \times 500$$

Calculation of the FOS/TAC ratio:

The FOS/TAC value is calculated as the ratio of those two results (FOS value divided by TAC value).

Table 2 shows the corresponding parameters of the control digester KF 1.

Table 3 shows the corresponding parameters of the test digester VF 2.

Table 4 shows the corresponding parameters of the test digester VF 3.

Table 5 shows the feeding rate of the three digesters and the corresponding biogas production reported to the feeding rate for the three digesters.

Table 6 shows the addition quantities of sodium bicarbonate to the test digester VF2.

Table 7 shows the addition quantities of sodium bicarbonate to the test digester VF3.

Table 8 shows the mean values of the biogas composition for the three digesters.

FIG. 1 shows the pH-values of the control digester KF1, and the test digesters 2 and 3 (VF2 and VF3) on the test period.

TABLE 2

Parameters of the control digester KF 1 without sodium bicarbonate addition.

| Time Days number | pH value mean value | FOS mg HAc · $l^{-1}$ | TAC mg CaCO$_3$ · $l^{-1}$ | FOS/TAC | Buffer capacity mmol · $l^{-1}$ | Volatile organic acids (Sr) g · kg$^{-1}$ FM |
|---|---|---|---|---|---|---|
| 21 | 7.60 | 2830 | 17075 | 0.17 | — | 1.07 |
| 28 | 7.62 | 4988 | 18700 | 0.27 | — | 2.55 |
| 35 | 7.64 | 3287 | 20525 | 0.16 | — | 1.07 |
| 42 | 7.57 | 3328 | 24600 | 0.14 | — | 0.90 |
| 49 | 7.53 | 3162 | 25000 | 0.13 | — | 1.07 |
| 56 | 7.54 | 2000 | 19038 | 0.10 | — | 0.99 |
| 63 | 7.58 | 1668 | 14225 | 0.12 | — | 0.92 |
| 70 | 7.55 | 1959 | 13638 | 0.14 | — | 0.97 |
| 77 | 7.56 | 2000 | 14463 | 0.14 | 288 | 1.11 |
| 84 | 7.44 | 1713 | 14310 | 0.12 | 343 | 1.43 |
| 91 | 7.32 | 1377 | 14055 | 0.10 | 327 | 1.51 |
| 98 | 7.26 | 1212 | 12450 | 0.10 | 289 | 1.34 |
| 105 | 7.18 | 1501 | 11319 | 0.13 | 263 | 1.41 |
| 112 | 7.17 | 1375 | 10347 | 0.13 | 243 | 1.17 |
| 119 | 7.15 | 1833 | 9683 | 0.19 | 227 | 1.00 |
| 126 | 7.32 | 1375 | 9124 | 0.15 | 218 | 0.93 |
| 133 | 7.21 | 1332 | 8138 | 0.16 | 200 | 0.83 |
| 140 | 7.14 | 1167 | 7727 | 0.15 | 187 | 0.71 |
| 147 | 7.10 | 1210 | 7289 | 0.17 | 176 | 0.97 |
| 154 | 7.06 | 1747 | 7109 | 0.25 | 169 | 2.44 |

TABLE 3

Parameters of the test digester VF 2 with sodium bicarbonate addition (day 77 and following).

| Time Days number | pH value mean value | FOS mg HAc · $l^{-1}$ | TAC mg CaCO$_3$ · $l^{-1}$ | FOS/TAC | Buffer capacity mmol · $l^{-1}$ | Volatile organic acids (Sr) g · kg$^{-1}$ FM |
|---|---|---|---|---|---|---|
| 0 | 7.63 | 3287 | 31500 | 0.10 | k.A. | 1.17 |
| 21 | 7.56 | 1959 | 18625 | 0.11 | k.A. | 1.11 |
| 28 | 7.56 | 4241 | 18750 | 0.23 | k.A. | 2.33 |
| 35 | 7.71 | 3079 | 19413 | 0.16 | k.A. | 1.19 |
| 42 | 7.49 | 2955 | 23663 | 0.12 | k.A. | 0.91 |
| 49 | 7.51 | 2955 | 23800 | 0.12 | k.A. | 1.12 |
| 56 | 7.42 | 2042 | 14263 | 0.14 | k.A. | 1.04 |
| 63 | 7.47 | 1834 | 13288 | 0.14 | k.A. | 0.95 |
| 70 | 7.46 | 1793 | 12138 | 0.15 | k.A. | 1.23 |
| 77 | 7.51 | 1585 | 13425 | 0.12 | 305 | 1.26 |
| 84 | 7.52 | 1294 | 14946 | 0.09 | 354 | 1.48 |
| 91 | 7.56 | 1336 | 16583 | 0.08 | 375 | 1.23 |
| 98 | 7.59 | 1046 | 15438 | 0.07 | 341 | 1.04 |
| 105 | 7.49 | 1461 | 13991 | 0.10 | 312 | 1.05 |
| 112 | 7.44 | 1627 | 13003 | 0.13 | 300 | 1.03 |
| 119 | 7.45 | 1460 | 12556 | 0.12 | 286 | 1.04 |
| 126 | 7.49 | 1251 | 11430 | 0.11 | 273 | 0.71 |
| 133 | 7.45 | 1248 | 10458 | 0.12 | 239 | 0.78 |
| 140 | 7.42 | 712 | 10022 | 0.07 | 225 | 0.59 |
| 147 | 7.38 | 1127 | 9411 | 0.12 | 216 | 0.84 |

TABLE 4

Parameters of the test digester VF 3 with sodium bicarbonate addition (day 77 and following).

| Time Days number | pH value mean value | FOS mg HAc · $l^{-1}$ | TAC mg CaCO$_3$ · $l^{-1}$ | FOS/TAC | Buffer capacity mmol · $l^{-1}$ | Volatile organic acids (Sr) g · kg$^{-1}$ FM |
|---|---|---|---|---|---|---|
| 0 | 7.59 | 3287 | 31500 | 0.10 | — | 1.17 |
| 21 | 7.59 | 1793 | 18988 | 0.09 | — | 1.23 |
| 28 | 7.56 | 4864 | 19200 | 0.25 | — | 2.54 |
| 35 | 7.68 | 3121 | 20638 | 0.15 | — | 1.11 |
| 42 | 7.64 | 2872 | 24788 | 0.12 | — | 0.98 |
| 49 | 7.58 | 2830 | 25413 | 0.11 | — | 1.19 |
| 56 | 7.60 | 2291 | 14913 | 0.15 | — | 1.08 |
| 63 | 7.62 | 1959 | 14125 | 0.14 | — | 1.01 |
| 70 | 7.56 | 2000 | 13438 | 0.15 | — | 1.02 |
| 77 | 7.59 | 2208 | 15563 | 0.14 | 353 | 1.25 |
| 84 | 7.62 | 1633 | 16813 | 0.10 | 387 | 1.45 |
| 91 | 7.69 | 1916 | 18511 | 0.10 | 424 | 1.87 |
| 98 | 7.68 | 1211 | 17308 | 0.07 | 383 | 1.43 |
| 105 | 7.61 | 1917 | 15475 | 0.12 | 353 | 1.62 |
| 112 | 7.54 | 3453 | 13438 | 0.26 | 337 | 2.40 |
| 119 | 7.48 | 5519 | 11358 | 0.49 | 311 | 4.63 |
| 126 | 7.65 | 1789 | 12341 | 0.15 | 287 | 1.05 |
| 133 | 7.59 | 1874 | 11351 | 0.17 | 265 | 1.09 |
| 140 | 7.49 | 1415 | 10783 | 0.13 | 251 | 1.17 |
| 147 | 7.46 | 2038 | 9795 | 0.21 | 237 | 2.22 |

TABLE 5 feeding rate of the three digesters and corresponding biogas production yield (production Nm3 biogas/day divided by kg of organic matter feeded).

| Time Days number | Organic matter feeding rate of the three digesters g oS · $l^{-1}$ · $d^{-1}$ | Biogas production yield Control KF1 Nm$^3$ · kg$^{-1}$oS | Biogas production yield Test digester VF2 Nm$^3$ · kg$^{-1}$oS | Biogas production yield Test digester VF3 Nm$^3$ · kg$^{-1}$oS | Hydraulic Residence Time of the three digesters KF1, VF2, VF3 Days |
|---|---|---|---|---|---|
| 28 | 1.04 | 0.375 | 0.389 | 0.397 | 267 |
| 35 | 1.05 | 0.736 | 0.719 | 0.735 | 267 |
| 42 | 2.01 | 0.596 | 0.584 | 0.618 | 139 |
| 49 | 2.01 | 0.671 | 0.672 | 0.669 | 139 |
| 56 | 2.56 | 0.655 | 0.658 | 0.671 | 111 |
| 63 | 2.5 | 0.667 | 0.68 | 0.705 | 111 |
| 70 | 3 | 0.67 | 0.663 | 0.682 | 93 |
| 77 | 3.02 | 0.656 | 0.648 | 0.669 | 93 |
| 84 | 3.5 | 0.668 | 0.67 | 0.672 | 80 |
| 91 | 4.09 | 0.667 | 0.676 | 0.677 | 70 |
| 98 | 4.59 | 0.638 | 0.643 | 0.641 | 62 |
| 105 | 5.17 | 0.624 | 0.632 | 0.645 | 56 |
| 112 | 5.52 | 0.624 | 0.649 | 0.638 | 51 |
| 119 | 6.01 | 0.628 | 0.635 | 0.606 | 47 |
| 126 | 2.54 | 0.761 | 0.768 | 0.841 | 112 |
| 133 | 3.51 | 0.645 | 0.662 | 0.688 | 81 |
| 140 | 4.52 | 0.606 | 0.611 | 0.631 | 63 |
| 147 | 5.52 | 0.605 | 0.614 | 0.608 | 51 |

TABLE 6 daily addition quantities of sodium bicarbonate to test digester VF2

| Days number D | TS Content VF2 g · kg$^{-1}$ | TS Content VF2 g | Daily added percentage Bicar % Bicar · TS$^{-1}$ · d$^{-1}$ | Added quantities g Bicar · d$^{-1}$ | oS Feeding rate of digester g oS · $l^{-1}$ · d$^{-1}$ | Added Bicar VF2 g · $l^{-1}$ · d$^{-1}$ |
|---|---|---|---|---|---|---|
| 77 | 47.4 | 498 | 0.500 | 2.49 | 3.0 | 0.237 |
| 84 | 44.9 | 472 | 1.000 | 4.72 | 3.5 | 0.449 |
| 91 | 48.5 | 509 | 1.000 | 5.09 | 4.1 | 0.485 |
| 98 | 52.1 | 547 | 0.500 | 2.74 | 4.6 | 0.261 |
| 105 | 60.2 | 632 | 0.125 | 0.79 | 5.2 | 0.075 |

TABLE 6-continued daily addition quantities of sodium bicarbonate to test digester VF2

| Days number D | TS Content VF2 g·kg$^{-1}$ | TS Content VF2 g | Daily added percentage Bicar % Bicar·TS$^{-1}$·d$^{-1}$ | Added quantities g Bicar·d$^{-1}$ | oS Feeding rate of digester g oS·l$^{-1}$·d$^{-1}$ | Added Bicar VF2 g·l$^{-1}$·d$^{-1}$ |
|---|---|---|---|---|---|---|
| 112 | 61.0 | 640 | 0.125 | 0.80 | 5.5 | 0.076 |
| 119 | 58.5 | 615 | 0.125 | 0.77 | 6.0 | 0.073 |
| 126 | 65.2 | 684 | 0.125 | 0.86 | 2.5 | 0.081 |
| 133 | 64.1 | 673 | 0.125 | 0.84 | 3.5 | 0.080 |
| 140 | 54.9 | 576 | 0.125 | 0.72 | 4.5 | 0.069 |
| 147 | 53.2 | 558 | 0.125 | 0.70 | 5.5 | 0.066 |

TABLE 7 daily addition quantities of sodium bicarbonate to test digester VF3

| Days number D | TS Content VF2 g·kg$^{-1}$ | TS Content VF3 g | Daily added percentage Bicar % Bicar·TS$^{-1}$·d$^{-1}$ | Added quantities g Bicar·d$^{-1}$ | oS Feeding rate of digester g oS·l$^{-1}$·d$^{-1}$ | Added Bicar VF3 g·l$^{-1}$·d$^{-1}$ |
|---|---|---|---|---|---|---|
| 77  | 49.5 | 520 | 0.500 | 2.60 | 3.0 | 0.248 |
| 84  | 53.0 | 557 | 1.000 | 5.57 | 3.5 | 0.530 |
| 91  | 54.1 | 568 | 1.000 | 5.68 | 4.1 | 0.541 |
| 98  | 58.9 | 618 | 0.500 | 3.09 | 4.6 | 0.295 |
| 105 | 69.6 | 731 | 0.125 | 0.91 | 5.2 | 0.087 |
| 112 | 66.9 | 703 | 0.125 | 0.88 | 5.5 | 0.084 |
| 119 | 63.4 | 666 | 0.125 | 0.83 | 6.0 | 0.079 |
| 126 | 69.1 | 726 | 0.125 | 0.91 | 2.5 | 0.086 |
| 133 | 71.3 | 749 | 0.125 | 0.94 | 3.5 | 0.089 |
| 140 | 59.7 | 626 | 0.125 | 0.78 | 4.5 | 0.075 |
| 147 | 55.6 | 584 | 0.125 | 0.73 | 5.5 | 0.069 |

TABLE 8

Biogas composition (mean values) for the three digesters during the period.

| Digester | CH$_4$ Vol. % | H$_2$S ppm | O$_2$ Vol % | CO$_2$ Vol. % | Σ Gas Vol. % |
|---|---|---|---|---|---|
| KF1 Control digester | 49.5 | 179 | 0.30 | 47.0 | 96.8 |
| VF2 Test digester    | 50.4 | 149 | 0.30 | 46.7 | 97.4 |
| VF3 Test digester    | 50.2 | 138 | 0.30 | 46.7 | 97.2 |

TABLE 9

Sodium concentrations of the organic feeding matter and of the digestion medium of the digesters.

| Sample | Day of sampling | Natrium content mg/kg |
|---|---|---|
| Organic feeding matter as Fresh mass (FM) | 88  | 357  |
| KF1 Control digester | 88  | 934  |
| VF2 Test digester    | 88  | 2415 |
| VF3 Test digester    | 88  | 2830 |
| KF1 Control digester | 147 | 697  |
| VF2 Test digester    | 147 | 2348 |
| VF3 Test digester    | 147 | 2780 |

As one can see in table 2, the high feeding rate of the control digester (KF 1), without the addition of a buffering reagent comprising sodium bicarbonate, has the consequence to continuously:

decrease the total inorganic carbon content (TAC) of the liquid of the digestion medium below 9000 mg of equivalent CaCO3/l of the liquid of the digestion medium, decrease the buffering capacity of the digestion medium to dangerous values down to 176 mmol/l, and decrease the pH value of the digestion medium from 7.6 down to also dangerous pH-value below 7.10.

showing that the digestion medium has no more the capacity to absorb such high organic matter feeding rates and is near to collapse.

Comparatively, the digesters 2 and 3 in which sodium bicarbonate has been added remain with:

total inorganic carbon (TAC) values above 9000 mg of equivalent CaCO3/l for the liquid, buffering capacity above 200 mmol/l and a good pH range of the digesters media above 7.38 for both of the digesters.

Figure 3:
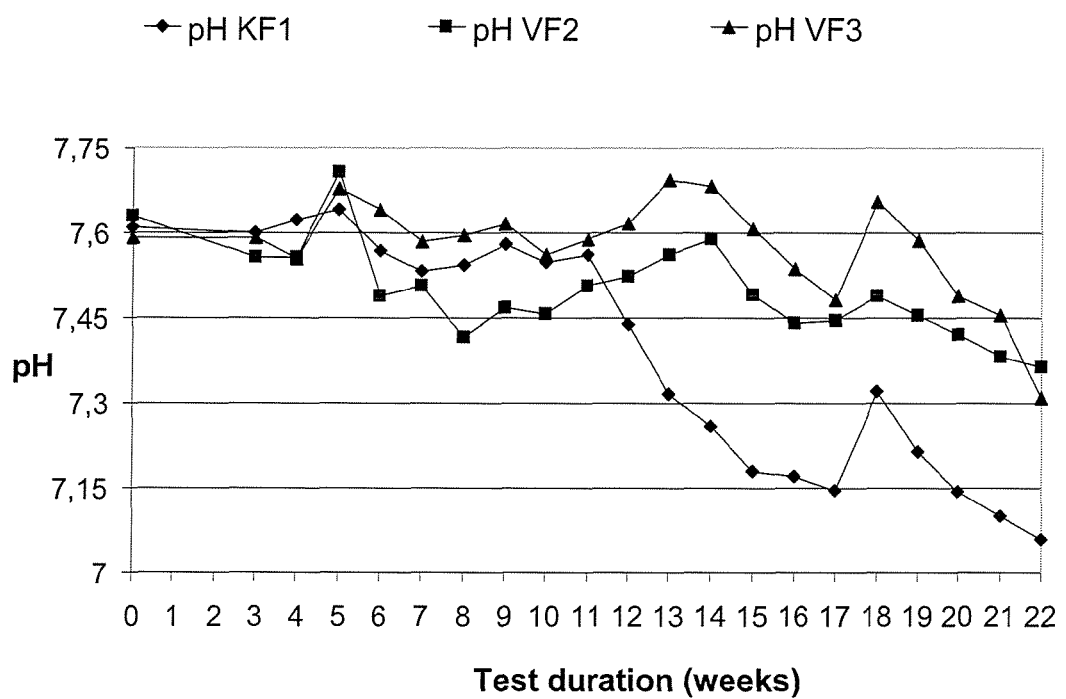
FIG. 3 is the plotted graph of the pH-values versus time of digesters 1 to 3 in example 1.

The FIG. 3 shows clearly a fast falling-down of the pH-value of the control digester at high feeding rate above 3.0 g oS/1/day specially after week number 11 (day 77), on 6 weeks time, the pH value can increase again when feeding rate is decreased to 2.5 g oS/1/day (week 18=day 126) but continue to sharply decreased down to pH 7.10 when feeding rate is increased again up to 5.5 g oS/1/day on three weeks time (up to week 22) showing an unstable digestion process.

Comparatively, the pH-values of test digesters 2 and 3 (VF2 and VF3), where the sodium bicarbonate is added to control a total inorganic carbon concentration above 9000 mg equivalent CaCO$_3$/l and the buffering capacity above 200 mmol/l, remain in the good pH range between 7.75 and 7.35 as can be observed in FIG. 1, even when the feeding rate is above 3.0 and up to 6.0 g oS/1/day.

Moreover, as shown in table 7 and 8:

the fermentation gas yields reported to the feeding organic matter content (oS) remain for test digesters higher than the control digester the global percentage of methane of the produced biogas in the period remains higher for test digesters 2 and 3 using sodium bicarbonate than the control digester, and the hydrogen sulphide content is significantly reduced from 179 ppm for the control digester down to 149 or 138 ppm for test digesters 2 and 3.

Example 2

In this example, the same three 10.5 liters digesters as in example 1 were used. Semi continuous trials according VDI recommendation 4630 (VDI-4630: VDI Society of energy engineering, fermentation of organic materials-2006) were performed.

The goal of that example was to test the recovery of a digester after a disruption accident with a down fall of pH-value provoked by an excess of acidic feeding material.

The organic feeding matter of the three digesters was a similar mixture (cow and pig manure/maize silage/grass silage) as to the one of example 1 and in same proportion as example 1. The characteristics of the organic feeding matter of example 2 are given in table 10. The addition took place on five days in the week, whereby the mean supplied quantity of organic matter refers to the entire week. The three digesters were fed five days per week with 60 g of organic feeding matter per day plus distilled water to remain at constant volume. This daily feeding load was 0.5 g oS·l$^{-1}$ d$^{-1}$ the first two weeks then increased to equivalent to 1 g oS·l$^{-1}$ d$^{-1}$, reported to the total volume of digester. A weekly analysis was performed on a 300 g sample of the digestion medium of the digesters.

The trial included the following phases:

degassing phase (day 0 to 40) for digesters 1 to 3 stabilization phase (day 40 to 75) for digesters 1 to 3 acidification phase (day 75 to 108) for digesters 2 and 3 convalescence phase (day 108 to 133) for digesters 2 and 3

TABLE 10

Characteristics and composition of the components of the organic matter mixture.

| Component | pH | Dry matter content $TS_{105}$ % FM | Organic content of the Dry matter oTS % TS | Organic content of the Dry matter oTS g·kg$^{-1}$ FM | Volatile organic acids Sr g·kg$^{-1}$ FM | Organic matter content oS g·kg$^{-1}$ FM | Organic matter content oS % FM |
|---|---|---|---|---|---|---|---|
| Cow & pig manure | 6.91 | 5.59 | 77.94 | 43.60 | 7.49 | 51.1 | 5.11 |
| Maize silage | 5.03 | 43.01 | 93.26 | 384.88 | 7.72 | 392.6 | 39.26 |

In the degassing phase, the three digesters were brought to similar and uniform operating conditions and characteristics of the digestion medium and gas quality.

Digester 1 was kept as a control digester without acid injection (acidification phase) and without sodium bicarbonate addition (convalescence phase).

Digesters 2 and 3, at the beginning of the acidification phase, were no more fed with the organic matter described above. In replacement, they were fed with 99.5% propionic acid, by means of pumps, to provoke a disruption accident. The daily acid feeding rate and quantities are given in table 11.

The acidification leads to a progressive pH down fall to pH 6.5 on day 108.

TABLE 11

Propionic acid feeding rates of digesters 2 and 3.

| Week | Starting Day | Propionic flow rate (ml·min$^{-1}$·d$^{-1}$) | Propionic acid quantities added (d$^{-1}$) | Propionic acid quantities added (g·d$^{-1}$) | Propionic acid quantities added reported to volume (g·l$^{-1}$·d$^{-1}$) |
|---|---|---|---|---|---|
| 1 | 75 | 0.9 | 4 | 3.6 | 0.34 |
| 2 | 82 | 2.0 | 4 | 8.0 | 0.76 |
| 3 | 89 | 3.9 | 4 | 15.6 | 1.49 |
| 4 | 96 | 5.2 | 6 | 31.2 | 2.97 |
| 5 | 103 | 5.1 | 12 | 61.2 | 5.83 |

On day 108 began the convalescence phase in which solid sodium bicarbonate, BICAR Tec from the Solvay Chemicals Company, was used to buffer the digestion media of digesters 2 and 3, to reach a total inorganic carbon content above 9000 mg equivalent CaCO$_3$/l and a buffering capacity higher than 200 mmol/l. The sodium bicarbonate added quantities are shown in table 12.

TABLE 12

Sodium bicarbonate additions to digesters 2 and 3.

| Digesters | Sodium bicarbonate quantity |
|---|---|
| Control digester | — |
| Test digester 2 | 90 g (first addition 60 g, and three hours later 30 g) |
| Test digester 3 | 90 g (first addition 60 g, and three hours later 30 g) |

Figure 4:
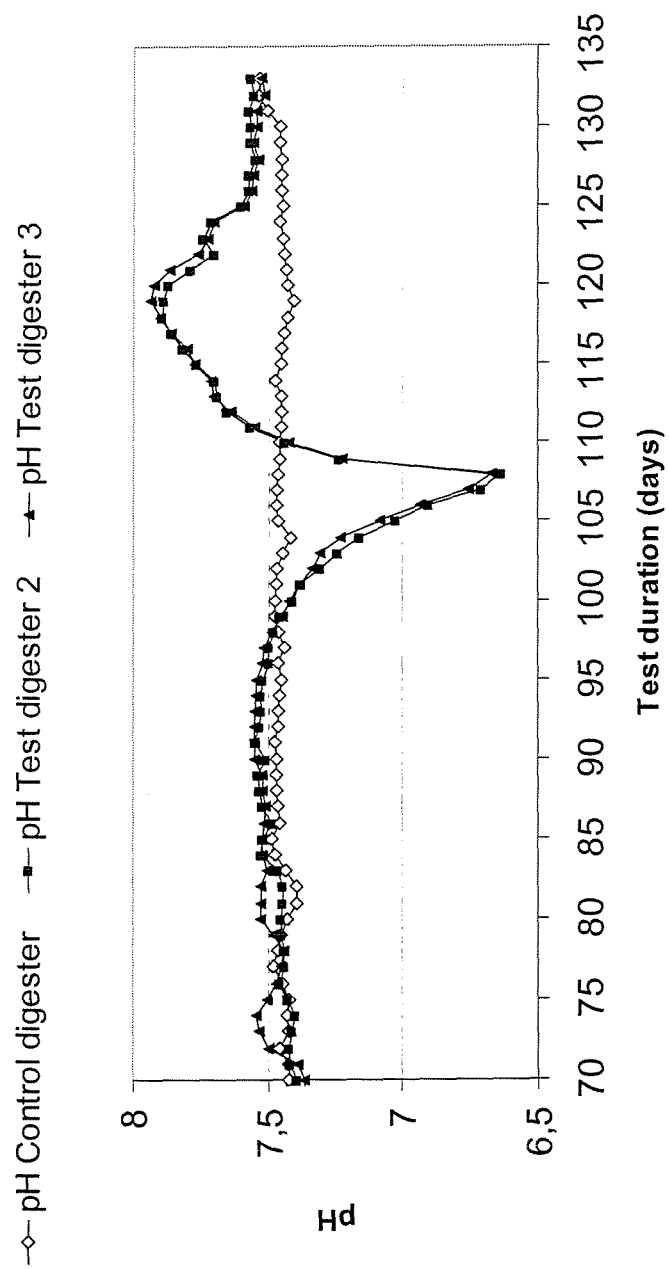
FIG. 4 is the plotted graph of the pH-values versus time of digesters 1 to 3 in example 2 during acidification and convalescence phases.

FIG. 4 shows the pH evolution of the three digesters on the acidification and convalescence phases.

Figure 5:
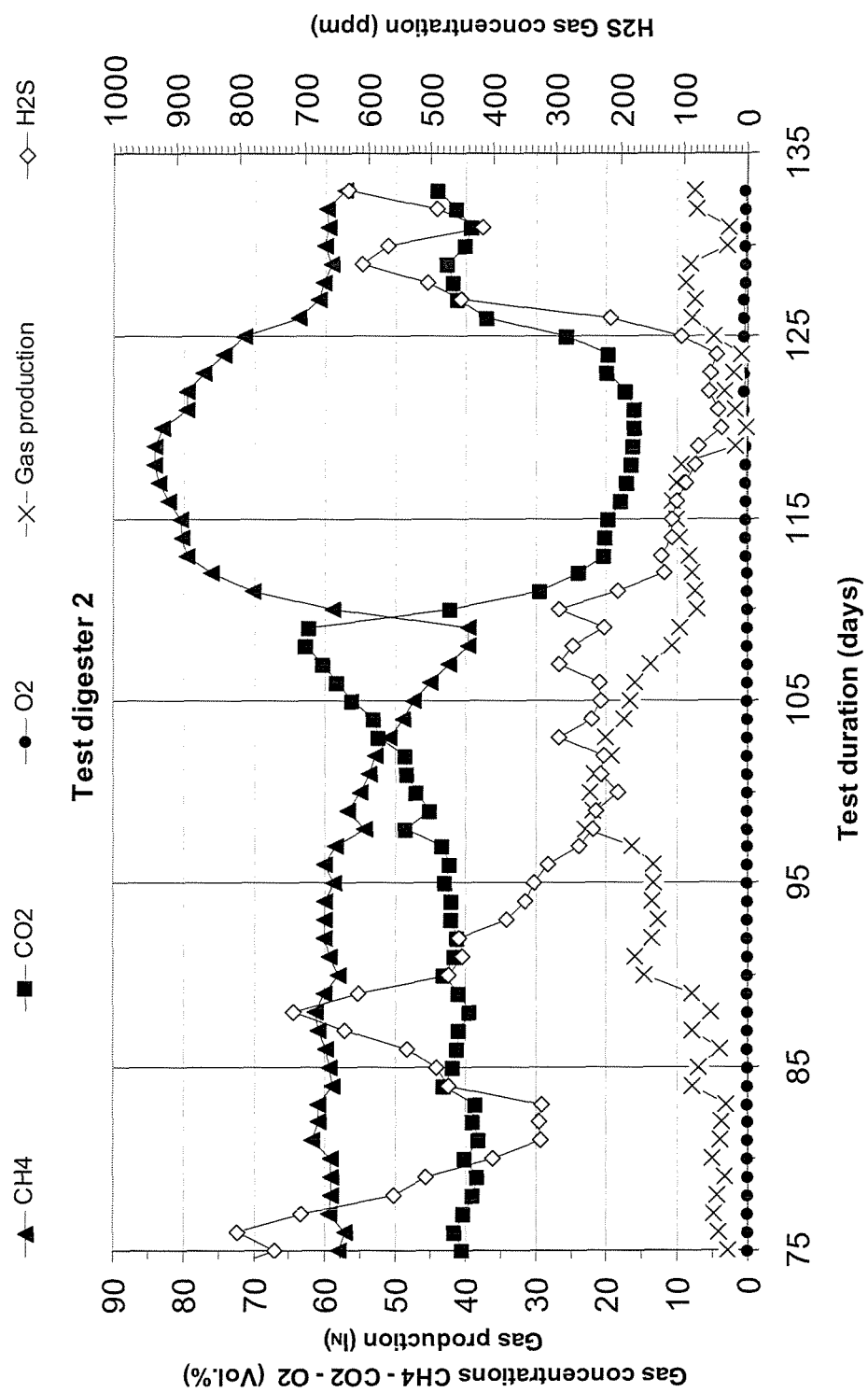
FIG. 5 is the plotted graph of the biogas composition in methane, carbon dioxide, hydrogen sulfide, and biogas production of digester 2 versus time in example 2.
Figure 6:
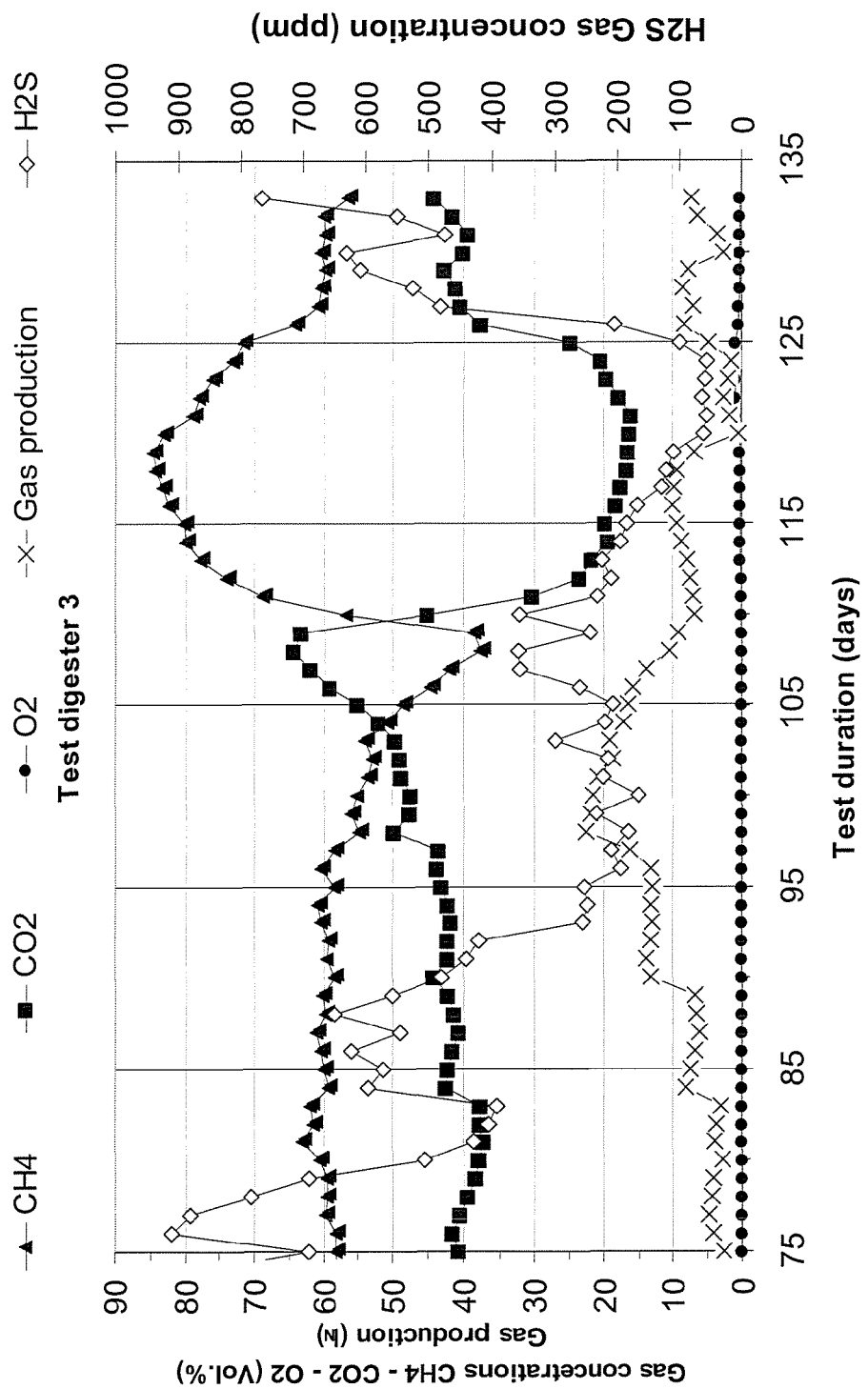
FIG. 6 is the plotted graph of the biogas composition in methane, carbon dioxide, hydrogen sulfide, and biogas production of digester 3 versus time in example 2.

FIG. 5 shows the biogas composition in methane, carbon dioxide, and hydrogen sulfide, and the biogas production in standard liters ($l_N$) of digester 2.

On FIG. 4 one can see that sodium bicarbonate addition is efficient to recover in less than 2 days pH values above 7.2, more particularly above 7.35 (day 110).

On FIG. 5 one can see that in the stronger acidification phase (days 96 to 108) the biogas production failed down, and the methane content of the biogas also failed down. In the convalescence period (after day 108), after sodium bicarbonate additions, the methane content of the biogas increased sharply up to 83 vol. % before stabilizing at 58 vol. %.

At day 120 organic matter was fed again into digesters 2 and 3. The pH value dropped by the acid effect of the feeding organic matter in the range about pH 7.45. After that methanegenic bacteria had adapted to the higher pH value, the digestion gas yield rose: the accumulated propionic acid was transformed to methane. When the organic matter was fed again after day 120, at a feeding load first at 0.5 g oS·l$^{-1}$·d$^{-1}$, the propionic acid of digesters 2 and 3 had probably restrained the hydrolysis. Therefore the organic matter was not converted immediately to biogas, but only from day 124. The cause may be in the adjustment time of the hydrolysis working bacteria to adapt again to the organic matter. After day 125, the pH values of the digesters 2 and 3 were similar to the control digester 1. From day 124 to 133 the feeding load was increased to 1.0 g oS·l$^{-1}$·d$^{-1}$, in order to reach the level of the control digester 1.

At the end of the convalescence phase, the digestion gas yield reached the level of the control digester 1. And the methane and carbon dioxide contents of digesters 2 and 3 were also similar to those of the biogas of digester 1. This shows the efficiency of a buffering reagent containing sodium bicarbonate when used at severe pH drops close to 6.5 without negative effect on the biological system in the digester to recover a good methane production yield.

Example 3

In this example, the organic matter (mixture of cow and pig manure, maize silage, grass silage) was identical to the one of example 1.

400 g of seeding sludge with the characteristics according VDI 4630, and 17.5 g of organic matter were put in polyethylene bottles, with different bone char quantities given in table 13. Each bottle test was doubled and referenced as KK x and KK x', with x designating the test number.

The bone char had a specific surface area of about 100 m$^2$/g. The chemical analysis of the main constituents and micronutrients of the bone char is given at tables 14.a and 14.b.

TABLE 13

Bone char quantities added.

| batch-bottle-number | bone char quantities in mg |
|---|---|
| KK 1 and KK 1' | 597.50 |
| KK 2 and KK 2' | 298.75 |

TABLE 13-continued

Bone char quantities added.

| batch-bottle-number | bone char quantities in mg |
|---|---|
| KK 3 and KK 3' | 149.38 |
| KK 4 and KK 4' | 74.69 |
| KK 5 and KK 5' | 37.34 |
| KK 6 and KK 6' | 18.67 |
| KK 7 and KK 7' | 9.34 |
| KK 8 and KK 8' | 4.67 |
| KK 9 and KK 9' | 2.33 |
| KK 10 and KK 10' | 1.17 |
| KK 11 and KK 11' | Control without bone char addition |

TABLE 14.a

Bone char chemical composition.

| Content | % of dry matter |
|---|---|
| Calcium, as CaO | 40.97 |
| Phosphorus as $P_2O_5$ | 33.46 |
| Sodium as $Na_2O$ | 1.24 |
| Magnesium as MgO | 0.99 |
| Potassium as $K_2O$ | 0.21 |
| Organic matter | 12.10 |
| Nitrogen | 0.90 |
| Ammonium-N ($NH_4$—N) | 0.00960 |

TABLE 14.b

Bone char chemical composition in micronutrients.

| Content | % of dry matter |
|---|---|
| As | 0.00001 |
| B | 0.00028 |
| Cd | 0.00001 |
| Chlorides | 0.12334 |
| Co | 0.00009 |
| Cr | 0.00104 |
| Cr VI | 0.00002 |
| Cu | 0.00028 |
| Fe | 0.12327 |
| Hg | 0.00000 |
| Mn | 0.00290 |
| Mo | 0.00002 |
| Ni | 0.00011 |
| Pb | 0.00055 |
| S | 0.00001 |
| Se | 0.05085 |
| Tl | 0.00002 |
| W | 0.00043 |
| Zn | 0.00895 |

Bottles 1 to 10' contained bone char. Bottles 11 and 11' were not fed with bone char, and were used as control.

The bottles were immerged in a controlled water bath at 35° C.

The biogas produced by each bottle was stored in a gas capacity and analyzed on a daily basis as in the example 1. After 28 days the determined biogas production was summed and compared.

Table 15 shows the obtained normal liters of biogas per kg of fresh matter or kg of the organic content of the organic matter, and the methane percentage in the biogas summed in the 28 days period.

TABLE 15

Biogas and methane batch productions after 28 days.

| Bottle number | $1_N$ gas · $kg^{-1}$ FM | $1_N CH_4$ · $kg^{-1}$ FM | $1_N$ gas · $kg^{-1}$ oS | $1_N CH_4$ · $kg^{-1}$ oS | $CH_4$ GasContent Vol. % |
|---|---|---|---|---|---|
| KK 1 | 147 | 66 | 516 | 233 | 45 |
| KK 1' | 146 | 67 | 513 | 236 | 46 |
| KK 2 | 133 | 62 | 469 | 219 | 47 |
| KK 2' | 144 | 65 | 507 | 228 | 45 |
| KK 3 | — | — | — | — | — |
| KK 3' | 145 | 65 | 511 | 228 | 45 |
| KK 4 | 145 | 65 | 511 | 230 | 45 |
| KK 4' | — | — | — | — | — |
| KK 5 | 131 | 58 | 462 | 205 | 44 |
| KK 5' | 135 | 62 | 476 | 218 | 46 |
| KK 6 | 148 | 67 | 521 | 237 | 45 |
| KK 6' | 142 | 68 | 500 | 238 | 48 |
| KK 7 | 153 | 72 | 537 | 252 | 47 |
| KK 7' | — | — | — | — | — |
| KK 8 | 132 | 59 | 464 | 206 | 44 |
| KK 8' | 134 | 60 | 472 | 213 | 45 |
| KK 9 | 133 | 64 | 467 | 224 | 48 |
| KK 9' | 147 | 68 | 516 | 238 | 46 |
| KK 10 | 129 | 60 | 455 | 211 | 46 |
| KK 10' | 141 | 65 | 495 | 228 | 46 |
| Control without bone char addition: | | | | | |
| KK 11 | 119 | 53 | 418 | 186 | 45 |
| KK 11' | 112 | 50 | 394 | 174 | 44 |

The table 15 shows that the potential biogas production of bottles 1 to 10' containing bone char, was about 455 (bottle KK10) to 537 (bottle KK7) normal liters of biogas per kilogram of organic content of the organic matter fed. The average value of the biogas production of bottles KK1 to KK10' was 494 normal liters per kilogram of organic content of the organic matter fed, and with an average methane content of 46 vol. %.

For the control bottles KK11 and KK11', the average value of the biogas production was 406 normal liters per kilogram of organic content of the organic matter fed, with an average methane content of 45 vol. %.

Therefore, in this example, the bone char enabled to increase the biogas production reported to the organic content of the organic matter of 22%, and the methane production of an average ratio of 26% compared to control bottles that didn't contain bone char.

Example 4

The process according the present invention has been applied in this example in two stages mesophile anaerobic digesters on a continuous mode.

In this example, two identical digesters and corresponding equipments, same as the ones of example 1 were used. To be operated as two stages units, each anaerobic digester was fed with the organic matter, or "hydrolysate", withdrawn from one hydrolyser-reactor.

The hydrolyser-reactor was made of transparent double-walled acrylic polymer (internal diameter 220 mm and height 305 mm), having a working volume of 10.5 liters. The hydrolyser-reactor was equipped with an anchor and bevel paddle agitator (height 280 mm, broadness 210 mm of the anchor and bevel paddle element, rotating speed 30 rpm, duration 2 minutes every 40 minutes).

The raw organic matter feeding the hydrolyser-reactor, was the same as in example 1 (see table 1 above) and in same proportion for the three components fed. The hydrolyser-reactor was maintained at 50° C. It was run in partially aerobic conditions provided by aerations with ambient air entering inside the reactor each time that part of the hydrolysate was removed to feed the digesters creating a negative pressure inside the reactor. The hydraulic residence time in hydrolyser-reactor was between 11 and 7 days, according the feeding rates of the digesters, i.e. according the daily withdrawals of the hydrolysates.

The feeding load of raw organic matter of the hydrolyser-reactor was in the range of 5 to 20 kg $oS \cdot m^{-3} \cdot d^{-1}$. The gas generated in the hydrolyser-reactor was stored and analyzed separately from the biogas produced in the anaerobic digesters.

Average measured values characteristics of the hydrolyzate that was used to feed the digesters are given in table 16.

The hydraulic residence times of the digesters were between 20 to 35 days according the feeding rates of organic matter (table 17: feeding rate of the digesters and biogas production yield production (Nm3 biogas/day divided by kg of organic matter fed)).

The preparatory degassing phase, which took four weeks, enabled to put at same level the anaerobic digester parameters. Each week, an equivalent of 200+/−100 g of aqueous medium of the anaerobic digesters were collected from the digesters for the analysis. The equivalent feeding rate from the hydrolyser was added to each digester after the degassing phase and water level completed to 10.5 liters.

TABLE 16

Characteristics of the hydrolyzate organic matter in the two steps proceeding

| Characteristics | Unit | hydrolyzate (feeding organic matter of digesters) average values |
|---|---|---|
| pH-value | — | 4.15 |
| Dry matter content (TS$_{105}$) | % FM | 15.58 |
| organic content of the Dry matter (oTS) | % TS | 93.42 |
| organic content of the dry matter (oTS) in $g \cdot kg^{-1}$ of fresh mass (FM) of organic matter | $g \cdot kg^{-1}$ FM | 145.55 |
| Volatile organic acids (Sr) in $g \cdot kg^{-1}$ of fresh mass | $g \cdot kg^{-1}$ FM | 3.37 |
| Organic content (oS) expressed in $g \cdot kg^{-1}$ of fresh mass of organic matter | $g \cdot kg^{-1}$ FM | 148.9 |
| Organic content (oS) | % FM | 14.89 |

The two two-stages units were used according the present invention, with the addition of sodium bicarbonate BICAR Tec from Solvay Company into the anaerobic digesters after the preparatory degassing phase and high driving phase. The corresponding quantities of sodium bicarbonate added to both anaerobic digesters (VF2 and VF3) are given at tables 18 and 19.

TABLE 17

Feeding rate of the two two stage digesters and corresponding biogas production yield (production Nm3 biogas/day divided by kg of organic matter fed).

| Time Days number | Organic matter feeding rate of the two digesters $g oS \cdot l^{-1} \cdot d^{-1}$ | Biogas production yield | | Hydraulic residence time VF2 &3 days |
|---|---|---|---|---|
| | | Test digester VF2 $Nm^3 \cdot kg^{-1}$ oS | Test digester VF3 $Nm^3 \cdot kg^{-1}$ oS | |
| 35 | 0.62 | 0.606 | 0.657 | 136 |
| 42 | 1.15 | 0.668 | 0.68 | 74 |
| 49 | 2.54 | 0.613 | 0.621 | 47 |
| 56 | 3.59 | 0.622 | 0.624 | 36 |
| 63 | 4.56 | 0.58 | 0.585 | 30 |
| 70 | 5.02 | 0.614 | 0.628 | 25 |
| 77 | 5.56 | 0.584 | 0.594 | 23 |
| 84 | 6.08 | 0.559 | 0.578 | 22 |
| 91 | 4.58 | 0.561 | 0.579 | 28 |
| 98 | 5.09 | 0.566 | 0.578 | 25 |
| 105 | 5.59 | 0.57 | 0.576 | 24 |
| 112 | 6.09 | 0.567 | 0.578 | 22 |

TABLE 18 daily addition quantities of sodium bicarbonate to two stage test digester VF2

| Days number d | Dry Content TS VF2 $g \cdot kg^{-1}$ | Dry Content TS VF2 g | Daily added percentage Bicar % Bicar · $TS^{-1} \cdot d^{-1}$ | Added quantities g Bicar · $d^{-1}$ | Added Bicar VF2 $g \cdot l^{-1} \cdot d^{-1}$ |
|---|---|---|---|---|---|
| 35 | 29.9 | 314 | 0.125 | 0.39 | 0.0374 |
| 42 | 28.8 | 302 | 0.125 | 0.38 | 0.036 |
| 49 | 30.4 | 320 | 0.175 | 0.56 | 0.0533 |
| 56 | 33.4 | 350 | 0.178 | 0.62 | 0.0594 |
| 63 | 36.5 | 384 | 0.184 | 0.71 | 0.0672 |
| 70 | 39.6 | 416 | 0.182 | 0.76 | 0.0721 |
| 77 | 45.7 | 480 | 0.166 | 0.79 | 0.0757 |
| 84 | 48.5 | 510 | 0.162 | 0.82 | 0.0784 |
| 91 | 54.7 | 574 | 0.125 | 0.72 | 0.0683 |
| 98 | 53.4 | 561 | 0.138 | 0.77 | 0.0737 |
| 105 | 55.9 | 587 | 0.146 | 0.86 | 0.0816 |
| 112 | 55.3 | 581 | 0.151 | 0.88 | 0.0836 |

TABLE 19 daily addition quantities of sodium bicarbonate to two stage test digester VF3

| Days number d | Dry Content TS VF3 $g \cdot kg^{-1}$ | Dry Content TS VF3 g | Daily added percentage Bicar % Bicar · $TS^{-1} \cdot d^{-1}$ | Added quantities g Bicar · $d^{-1}$ | Added Bicar VF3 $g \cdot l^{-1} \cdot d^{-1}$ |
|---|---|---|---|---|---|
| 35 | 31.4 | 330 | 0.125 | 0.41 | 0.0393 |
| 42 | 32.5 | 342 | 0.125 | 0.43 | 0.0407 |
| 49 | 33 | 347 | 0.175 | 0.61 | 0.0578 |
| 56 | 35.2 | 370 | 0.178 | 0.66 | 0.0627 |
| 63 | 38.4 | 403 | 0.184 | 0.74 | 0.0707 |
| 70 | 42.5 | 446 | 0.182 | 0.81 | 0.0773 |
| 77 | 48.2 | 506 | 0.166 | 0.84 | 0.0797 |
| 84 | 50.5 | 530 | 0.162 | 0.86 | 0.0816 |
| 91 | 54.3 | 570 | 0.125 | 0.71 | 0.0679 |
| 98 | 52.8 | 554 | 0.138 | 0.77 | 0.0729 |

TABLE 19-continued daily addition quantities of sodium bicarbonate to two stage test digester VF3

| Days number d | Dry Content TS VF3 g·kg$^{-1}$ | Dry Content TS VF3 g | Daily added percentage Bicar % Bicar· TS$^{-1}$·d$^{-1}$ | Added quantities g Bicar· d$^{-1}$ | Added Bicar VF3 g·l$^{-1}$·d$^{-1}$ |
|---|---|---|---|---|---|
| 105 | 55 | 577 | 0.146 | 0.84 | 0.0802 |
| 112 | 56.4 | 592 | 0.151 | 0.89 | 0.0852 |

The two anaerobic digesters were maintained at a temperature of 38+/−1° C. and fed at a feeding load from 0.62 to 6.09 kg oS·m$^{-3}$·d$^{-1}$ on a daily base, 5 days per week for 8 weeks. And 4 weeks with a daily base, 7 days per week with a feeding load from 4.58 to 6.09 kg oS·m$^{-3}$·d$^{-1}$. The hydraulic residence times in the two identical digesters were between 22 and 36 days according the feeding rates. The produced biogas in each digester was collected as in example 1, in aluminum-coated polyethylene gas bags of 100 liters useful capacity. The composition of the biogas for each digester was analyzed as in example 1, on calibrated multi gas analyzer Biogas Monitor BM 2000.

Taking into account the high feeding rates of 4.56 to 6.09 kg oS·m$^{-3}$·d$^{-1}$, the biogas yield versus organic load was particularly good with values between 0.56 to 0.63 Nm3·kg-1·oS during all the high feeding period.

Comparatively industrial anaerobic digester not run as present invention and at a lower feeding rates (3.0+/−0.5 kg oS·m$^{-3}$·d$^{-1}$) has common biogas yield values between 0.34 to 0.64 Nm$^3$·kg oTS, with mean values of 0.58 Nm$^3$·kg oTS.

The measured H$_2$S concentrations of the produced biogas of digesters 1 and 2 (respectively VF2 and VF3) run in two stages unit and/or according present invention were measured between 100 to 200 ppm which are particularly low.

Should the disclosure of any patents, patent applications, and publications which are incorporated herein by reference conflict with the description of the present application to the extent that it may render a term unclear, the present description shall take precedence.

The invention claimed is:

1. A process for the production of a biogas containing methane from an organic matter amenable to anaerobic digestion, comprising feeding an anaerobic digester with said organic matter, said anaerobic digester containing an aqueous medium comprising microorganisms capable of digesting said organic matter to obtain a digestion medium comprising an aqueous liquid, converting part of said organic matter into biogas, wherein:
the total inorganic carbon concentration of the aqueous liquid of the digestion medium is maintained during anaerobic digestion above 9500 mg of equivalent CaCO3/l,
the buffering capacity of the digestion medium is maintained above 200 mmol/l by addition of a buffering reagent comprising sodium bicarbonate to the digestion medium,
the anaerobic digester is operated continuously, and
the feeding rate of the anaerobic digester with said organic matter is at least 4 kg of dry organic matter per cubic meter of digestion medium per day.

2. The process according to claim 1, wherein the buffering capacity of the digestion medium is at most 500 mmol/l.

3. The process according to claim 1, wherein the feeding rate of the anaerobic digester with said organic matter is at least 4.1 kg of dry organic matter per cubic meter of digestion medium per day.

4. The process according to claim 1, wherein the aqueous liquid of the digestion medium has a volatile organic acids content being maintained to less than 3000 mg HAc/l by addition of the buffering reagent comprising sodium bicarbonate to the digestion medium.

5. The process according to claim 1, wherein the addition of the buffering reagent comprising sodium bicarbonate is limited so that the aqueous liquid of the digestion medium has a sodium concentration of less than 60 g/l.

6. The process according to claim 1, wherein the digestion medium has a sodium concentration of at least 0.6 g/l.

7. The process according to claim 1, wherein the pH of the digestion medium is maintained at a value from 6.90 to 7.90.

8. The process according to claim 7, wherein in the event that the pH-value of the digestion medium falls below 6.5, another buffering reagent comprising a carbonate selected from the group consisting of calcium carbonate, magnesium carbonate, sodium carbonate, and any combinations thereof, is introduced into the digestion medium to increase the pH-value up to at least 6.5, and then the buffering reagent comprising sodium bicarbonate is introduced into the digestion medium to increase the pH-value up to at least 6.90.

9. The process according to claim 1, wherein the buffering reagent comprising sodium bicarbonate comprises a sodium bicarbonate powder which has a particle size distribution such that at least 10% of the particles have a diameter of more than 100 μm.

10. The process according to claim 1, wherein a nutrient additive is introduced into the digestion medium.

11. The process according to claim 1, wherein several anaerobic digesters are operated in series or in parallel.

12. The process according to claim 1, wherein the organic matter amenable to anaerobic digestion feeding the anaerobic digester is withdrawn from a hydrolyser-reactor.

13. The process according to claim 12, wherein said hydrolyser-reactor is operated at acidic pH between 3.8 and 5.8, at a temperature of 40 to 55° C., with a hydraulic residence time between 3 to 11 days, at a feeding rate of from 5 to 20 kg of dry organic matter per cubic meter of hydrolyser-reactor medium per day.

14. The process according to claim 1, further comprising:
collecting the biogas containing methane,
burning the biogas with a gas containing oxygen to form an exhaust gas containing acidic gas matter,
injecting sodium bicarbonate solid particles in the exhaust gas, and
carrying out a neutralization of part of the acidic gas matter of the exhaust gas with said sodium bicarbonate solid particles to form corresponding sodium salts and a partially purified exhaust gas.

15. The process according to claim 13, further comprising:
collecting the sodium salts from the partially purified exhaust gas,
wherein part of the collected sodium salts is further used as the buffering reagent comprising sodium bicarbonate or used as another buffering reagent comprising a carbonate selected from the group consisting of calcium carbonate, magnesium carbonate, sodium carbonate, and combinations thereof added to the digestion medium.

16. The process according to claim 1, wherein the addition of the buffering reagent comprising sodium bicarbonate reduces hydrogen sulfide content of the biogas.

17. The process according to claim 1, wherein the buffering capacity of the digestion medium is maintained above 250 mmol/l.

18. The process according to claim 3, wherein the feeding rate of the anaerobic digester with said organic matter is at least 4.5 kg of dry organic matter per cubic meter of digestion medium per day.

19. The process according to claim 1, wherein the organic matter fed to said anaerobic digester is a mix of cereals silage, grass silage, and animal manure.

20. The process according to claim 19, wherein said animal manure is selected from the group consisting of cow, cattle, swine, sheep, goat, poultry, camel, alpaca, dromedary, llama, equidae manure, and combinations thereof.

21. The process according to claim 1, wherein the organic matter fed to said anaerobic digester is a mixture of maize silage, grass silage, and an animal manure selected from the group consisting of pig manure, cow manure, and combinations thereof.

* * * * *